(12) United States Patent
Ryoo et al.

(10) Patent No.: US 9,579,295 B2
(45) Date of Patent: *Feb. 28, 2017

(54) DOSAGE FORM FOR INSERTION INTO THE MOUTH

(71) Applicant: NAL Pharmaceutical Group Limited, Causeway Bay (HK)

(72) Inventors: Je Phil Ryoo, Princeton, NJ (US); Chun Kwong Chu, Shatin (HK); Zheng Wang, Bridgewater, NJ (US)

(73) Assignee: NAL PHARMACEUTICAL GROUP LIMITED, Causeway Bay (HK)

( * ) Notice: Subject to any disclaimer, the term of this patent is extended or adjusted under 35 U.S.C. 154(b) by 0 days.

This patent is subject to a terminal disclaimer.

(21) Appl. No.: 14/803,757

(22) Filed: Jul. 20, 2015

(65) Prior Publication Data

US 2015/0320695 A1 Nov. 12, 2015

Related U.S. Application Data

(60) Continuation of application No. 14/280,033, filed on May 16, 2014, now Pat. No. 9,114,073, which is a (Continued)

(51) Int. Cl.
*A61K 9/70* (2006.01)
*A61K 38/06* (2006.01)
(Continued)

(52) U.S. Cl.
CPC ............ *A61K 9/7015* (2013.01); *A61K 9/006* (2013.01); *A61K 9/0056* (2013.01);
(Continued)

(58) Field of Classification Search
None
See application file for complete search history.

(56) References Cited

U.S. PATENT DOCUMENTS 3,598,122 A 8/1971 Zaffaroni
3,784,390 A 1/1974 Hijiyla et al.
(Continued)

FOREIGN PATENT DOCUMENTS

WO WO 2007/125533 A2 11/2007
WO WO 2009/029543 A1 3/2009

OTHER PUBLICATIONS

C.D. Mullins, et al., "Triptans for Migrane Therapy: A Comparison Based on Number Needed to Treat and Doses Needed to Treat", vol. 11, No. 5 Jun. 2005 Journal of Managed Care Pharmacy, pp. 397-402.
(Continued)

*Primary Examiner* — Robert A Wax
*Assistant Examiner* — Melissa Mercier
(74) *Attorney, Agent, or Firm* — Lucas & Mercanti, LLP

(57) ABSTRACT

Oral dosage forms as a biodegradable, water soluble film for delivering pharmaceutically active agents, to patients through insertion into the mouth of patient and methods for administering pharmaceutically active agents to patients by insertion into the mouth to provide selective uptake of said agents through the mucosa and thus avoiding the gastrointestinal tract.

24 Claims, 3 Drawing Sheets

Related U.S. Application Data continuation of application No. 13/655,194, filed on Oct. 18, 2012, now Pat. No. 8,771,736, which is a division of application No. 12/608,445, filed on Oct. 29, 2009, now Pat. No. 8,715,715.

(60) Provisional application No. 61/110,775, filed on Nov. 3, 2008.

(51) Int. Cl.

| | | |
|---|---|---|
| A61K 9/00 | (2006.01) | |
| A61K 31/00 | (2006.01) | |
| A61K 31/4196 | (2006.01) | |
| A61K 47/26 | (2006.01) | |
| A61K 47/32 | (2006.01) | |
| A61K 47/36 | (2006.01) | |
| A61K 47/38 | (2006.01) | |
| A61K 9/20 | (2006.01) | |
| A61K 31/192 | (2006.01) | |
| A61K 31/4045 | (2006.01) | |
| A61K 31/422 | (2006.01) | |
| A61K 31/4439 | (2006.01) | |
| A61K 31/445 | (2006.01) | |
| A61K 31/495 | (2006.01) | |
| A61K 31/55 | (2006.01) | |
| A61K 38/05 | (2006.01) | |
| A61K 31/465 | (2006.01) | |
| A61K 31/78 | (2006.01) | |
| A61K 31/196 | (2006.01) | |
| A61K 31/421 | (2006.01) | |
| A61K 31/4468 | (2006.01) | |

(52) U.S. Cl.
CPC .......... *A61K 9/0095* (2013.01); *A61K 9/2018* (2013.01); *A61K 9/2027* (2013.01); *A61K 9/7007* (2013.01); *A61K 31/00* (2013.01); *A61K 31/192* (2013.01); *A61K 31/196* (2013.01); *A61K 31/4045* (2013.01); *A61K 31/4196* (2013.01); *A61K 31/421* (2013.01); *A61K 31/422* (2013.01); *A61K 31/445* (2013.01); *A61K 31/4439* (2013.01); *A61K 31/4468* (2013.01); *A61K 31/465* (2013.01); *A61K 31/495* (2013.01); *A61K 31/55* (2013.01); *A61K 31/78* (2013.01); *A61K 38/05* (2013.01); *A61K 38/06* (2013.01); *A61K 47/26* (2013.01); *A61K 47/32* (2013.01); *A61K 47/36* (2013.01); *A61K 47/38* (2013.01)

(56) References Cited

U.S. PATENT DOCUMENTS

| | | |
|---|---|---|
| 4,379,454 A | 4/1983 | Campbell et al. |
| 4,568,343 A | 2/1986 | Leeper et al. |
| 4,623,394 A | 11/1986 | Nakamura et al. |
| 4,865,848 A | 9/1989 | Cheng et al. |
| 4,900,555 A | 2/1990 | Cheng et al. |
| 4,956,171 A | 9/1990 | Chang |
| 5,534,554 A | 7/1996 | Katz et al. |
| 6,541,030 B2 | 4/2003 | Vaghefi |
| 6,552,024 B1 | 4/2003 | Chen et al. |
| 6,747,014 B2 | 6/2004 | Teng et al. |
| 6,887,307 B1 | 5/2005 | Scott et al. |
| 6,953,790 B2 | 10/2005 | Burgey et al. |
| 6,956,298 B2 | 10/2005 | Kitajima et al. |
| 7,018,621 B2 | 3/2006 | Hale et al. |
| 7,025,983 B2 | 4/2006 | Leung et al. |
| 7,235,545 B2 | 6/2007 | Burgey et al. |
| 7,431,942 B2 | 10/2008 | Shimizu et al. |
| 7,727,552 B1 | 6/2010 | Ukai et al. |
| 8,105,625 B2 | 1/2012 | Rajewski et al. |
| 8,715,715 B2 * | 5/2014 | Ryoo .................. A61K 9/0056 424/435 |
| 8,771,736 B2 * | 7/2014 | Ryoo .................. A61K 9/0056 424/484 |
| 9,114,073 B2 * | 8/2015 | Ryoo .................. A61K 9/0056 |
| 9,114,074 B2 * | 8/2015 | Ryoo .................. A61K 9/0056 |
| 9,114,075 B2 * | 8/2015 | Ryoo .................. A61K 9/0056 |
| 2002/0015730 A1 | 2/2002 | Hoffmann et al. |
| 2004/0248846 A1 | 12/2004 | Quay et al. |
| 2007/0225272 A1 | 9/2007 | Burgey et al. |
| 2008/0113966 A1 | 5/2008 | Burgey et al. |
| 2008/0280857 A1 | 11/2008 | Burgey et al. |

OTHER PUBLICATIONS

Mitsubishi-Kagaku Foods Corp. 2002, "Introduction of Sugar Esters" p. 1-4, //www.mfc.co.jp/english/whatsse.htm.

S. Swan et al. "Pharmacokinetic Profile of Rizatriptan 10-mg Tablet and 10-mg Orally Disintegrating Tablet Administered With or Without Water in Healthy Subjects; An Open-Label, Randomized, Single-Dose, 3-Period Crossover Study", J. Clin Pharmacol 2006, 46:172-178.

Aqil et al., "Status of terpenes as skin penetration enhancers."; Drug Discovery Today (2007); vol. 12; Issue 23-24; pp. 1061-1067.

Femenia-Font A., et al; "Effect of chemical enhancers on the in vitro percutaneous absorption of sumatriptan succinate"; Eur. J. Pharm Biopharm. Sep. 2005; 61(1-2): 50-5.

Okamoto, Hirokazu et al.; "Effect of Sucrose Fatty Acid Esters on Transdermal Permeation of Lidocaine and Ketoprofen"; Biol. Pharm. Bull. 28(9) 1689-1694 (2005).

Balaguer-Fernandez, et al. "Sumatriptan Succinate Transdermal Delivery Systems for the Treatment of Migrane" Journ. Pharmac. Sciences, vol. 97 No. 6, Jun. 2008; pp. 2102-2109.

Tfelt-Hansen, "Triptans in Migraine—A Comparative Review of Pharmacology, Pharmacokinetics and Efficacy" Adis Int'l Ltd., Drugs Dec. 2000; 60(6); 1259-1287.

Szuts, Angela et al., "Study of Thermo-Sensitive Gel-Forming Properties of Sucrose Stearates", IPEC-Americas, Inc., J. Excipients and Food Chem. 1(2) 2010 pp. 13-20.

Nakada, Yuichiro et al. "The Effect of Additives on the Oral Mucosal Absorption of Human Calictonin in Rats" J. Pharmacobio-Dyn, 111, 395-401 (1988).

* cited by examiner

DOSAGE FORM FOR INSERTION INTO THE MOUTH

CROSS REFERENCES TO RELATED APPLICATIONS

This application is a continuation of U.S. patent application Ser. No. 14/280,033 filed May 16, 2014, which is a continuation of U.S. patent application Ser. No. 13/655,194 filed Oct. 18, 2012, which is a divisional of U.S. patent application Ser. No. 12/608,445 filed Oct. 29, 2009, which claims the benefit of priority of U.S. Provisional Application No. 61/110,775 filed on Nov. 3, 2008, the contents of each of which are hereby incorporated by reference in its entirety.

FIELD OF THE INVENTION

The present invention relates to oral dosage forms for insertion into the mouth for selective adsorption by the mucosal tissue, particularly for administration of medicinal agents where fast onset of action is desirable for medicines such as but not limited to anti-migraine agents. In particular, the present invention relates to pharmaceutical formulation of the anti-migraine drugs in the class of triptans.

BACKGROUND OF THE INVENTION

Migraine is one of the most common neurological conditions. Migraine headaches affect a large portion of the U.S. population and are more prevalent than diabetes, epilepsy and asthma combined. Migraine is more than just a headache; it can be a debilitating condition which has a considerable impact on the quality of life of sufferers and their families. Attacks can be completely disabling, forcing the sufferer to abandon everyday activities. Even in symptom-free periods, sufferers may live in fear of the next attack. Migraine attacks normally last between 4 and 72 hours and sufferers are usually symptom free between attacks.

Migraine is believed to be caused by the release of a chemical called serotonin or 5HT into the bloodstream. This causes the pain neurons in the blood vessel wall to become irritated. Exactly what causes the release of serotonin is still a subject for research and debate. However, certain factors have been identified which can trigger attacks in susceptible people. Some of these are stress or sometimes the relief of stress, lack of food or infrequent meals, foods containing ingredients such as mono-sodium glutamate, caffeine and chocolate, or alcohol (especially red wine), overtiredness (physical or mental), changes in sleep patterns (e.g., late nights or a weekend lie-in), or hormonal factors (e.g., monthly periods, the contraceptive pill or hormonal changes in males and females as they age).

Migraines are more common than cluster headaches, and have been studied more extensively. In addition, a better and more effective set of drugs have been developed to treat migraines, than cluster headache. For those reasons, the discussion below focuses mainly on migraines, rather than cluster headaches.

"Cluster headaches" were given that name because they tend to occur in episodic clusters, with a cluster cycle usually lasting 4 to 8 weeks. In some patients, a cluster occurs only once in a lifetime; in other patients, a cluster may occur roughly once a year, with periods of complete remission between attacks; and, in the roughly 10% of patients who are chronic sufferers, there are no significant periods of remission. As opposed to migraines (which occur in women at roughly 3 times the rates as in men), cluster headaches are more prevalent in men than in women, by a factor of about 5:1 or higher.

Migraines and cluster headaches are both classified as "recurrent primary headaches". They are recurrent, since they recur with sufficient frequency to seriously interfere with the health and quality of life of a patient, to a point of requiring and demanding medical attention, as opposed to just taking aspirin or similar over-the-counter analgesics and lying down till it passes. They are also regarded as "primary" headaches, since they usually arise as a primary adverse biologic condition, independently of other causative medical conditions such as tumors, sinus or other infections, bleeding problems, etc.

Current methods for administering anti-migraine pharmaceuticals have major limitations. For example, due to degradation in the gastrointestinal track and low adsorption of the drug, oral ingestible dosage forms of anti-migraine medications have to be administered in large doses of about 20-100 mg. These high doses may causes nausea, vomiting and other unwanted adverse side effects. Many anti-migraine agents are subject to pre-systemic and first pass metabolism. Because of this, it is estimated that as little as 2-10% of the active unchanged drug actually reaches the blood stream. In fact this causes delay in the effectiveness of the drug as a treatment or prophylaxis of the disorder in the patient. Likewise, intranasal administration of anti-migraine agents is hampered with significant limitations due to reduced absorption and low bioavailability.

Injectable and nasal spray forms of anti-migraine agents are also available for the treatment of migraines. Although parenteral administration of anti-migraine agents into the blood stream allows for a lower dose as compared to other non-injectable methods of administration, the inconvenience of an office visit for an injection or problems with the self-administration of injectables are self evident.

In the past, migraine headaches have been treated by use of rizaptriptan, sumatriptan, zolmitriptan or other triptan drugs. These drugs have basically been administered using conventional dosage forms such as pills or capsules or for sumatriptan through injection and nasal spray. The problem with the gastrointestinal (GI) administered triptan anti-migraine pharmaceutical agents is that they have a low GI bioavailability of approximately 15% to 40% and cause GI irritations. In addition, it is important that these drugs be delivered rapidly to a patient to prevent or treat the onset of a migraine headache and give immediate relief. The delay in release of the drug from the dosage form into and the bioavailability of the drug after administration causes undue suffering in the patient which is especially acute with patients suffering from migraine headaches. Therefore, what is needed are formulations that are effective for treating migraines which allow rapid drug release and bioavailability while avoiding the GI irritations which occur with the known administration of anti-migraine medications.

Triptans have been developed for the acute treatment of migraine. These medicines are available in the form of tablets for eletriptan, frovatriptan, sumatriptan, zolmitriptan, naratriptan, rizatriptan and almotriptan. These products are intended to be taken in amounts up to a maximum of 5 to 200 mg per day. Table A summarizes dosing regimens for triptan products.

TABLE A

Triptan Dosing Regimens

| Generic Name | Dose | Brand Name | Maximum 24 hour Dose |
|---|---|---|---|
| Almotriptan | 12.5 mg | Axert | 12.5 mg |
| Eletriptan | 40 mg | Relpax | 80 mg |
| Frovatriptan | 2.5 mg | Frova | 7.5 mg |
| Naratriptan | 2.5 mg | Amerge | 5.0 mg |
| Rizatriptan | 10 mg | Maxalt | 30 mg |
| Sumatriptan | 100 mg | Imitrex | 200 mg |
| Sumatriptan injection | 6 mg | Imitrex | 6 mg |
| Sumatriptan nasal spray | 20 mg | Imitrex | 40 mg |
| Zolmitriptan | 2.5 mg | Zomig | 10 mg |
| Zolmitriptan | 5 mg | Zomig ZMT | 10 mg |
| Zolmitriptan | 5 mg | Zomig ZMT | 10 mg |

Oral form unless otherwise noted.

SUMMARY OF INVENTION

We have discovered a water soluble matrix which can be incorporated into a solid, film or liquid oral dosage form for insertion into the mouth as a means for effectively delivering to, and transporting pharmaceutical active agents selectively through the oral mucosal tissue into the patient. This water soluble matrix system delivers the pharmaceutical active agent effectively and rapidly into the body through the mucous membranes in the mouth. While this system is effective for delivering pharmaceutically active agents, this system is ideally suited for delivering pharmaceutically active agents which treat or prevent migraine headaches, especially the triptans which include eletriptan, frovatriptan, sumatriptan, zolmitriptan, naratriptan, rizatriptan and almotriptan. Preferred triptans for selective oral mucosal delivery are rizaptriptan, sumatriptan and zolmitriptan.

The oral dosage matrix of this invention transports these pharmaceutically active agents selectively through the mucous membrane in the mouth bypassing the GI system so as to avoid GI irritations and deactivation of the active agent in the GI track. Without GI inactivation, less active agent is needed to produce a therapeutic result. In addition, the oral dosage matrix of this invention rapidly releases the pharmaceutically active agent for transport quickly into the blood stream of the patient. Transport of the active agents selectively through the mucus membranes of the mouth is facilitated by incorporating one or more fatty acid esters of sucrose having a combined hydrophilic lipophilic balance (HLB) of about 8 to about 16 with the active agent to form the matrix. The fatty acid esters of sucrose are an effective absorption enhancer. The oral dosage matrix of this invention produces improved bioavailability and delivery of the pharmaceutical active agent with rapid onset of therapeutic effectiveness for the patient. Rapid release and rapid, efficient absorption is particularly important for patients suffering from migraine headaches.

The oral dosage matrix, pharmaceutically active agent and fatty acid ester of sucrose, may be added to additional ingredients to produce dosage forms such as a film, a rapid releasing solid such as a powder or granule, a tablet, and also a liquid which contain an effective amount of the pharmaceutically active agent to relieve a migraine and related symptoms or act as a prophylactic disbursed therein. In accordance with this invention, this oral dosage matrix when incorporated into a tablet, film or other solid dosage form or solid dosage unit may further comprise a polymeric mixture of polyvinyl pyrrolidone and a polymeric alginate. This solid dosage form is of a size suitable for insertion into the mouth. In particular, this solid dosage form is particularly advantageous for administration of anti migraine agents which function, either or both, as a prophylactic and a treatment of migraine headaches.

DETAILED DESCRIPTION

Figure 1:
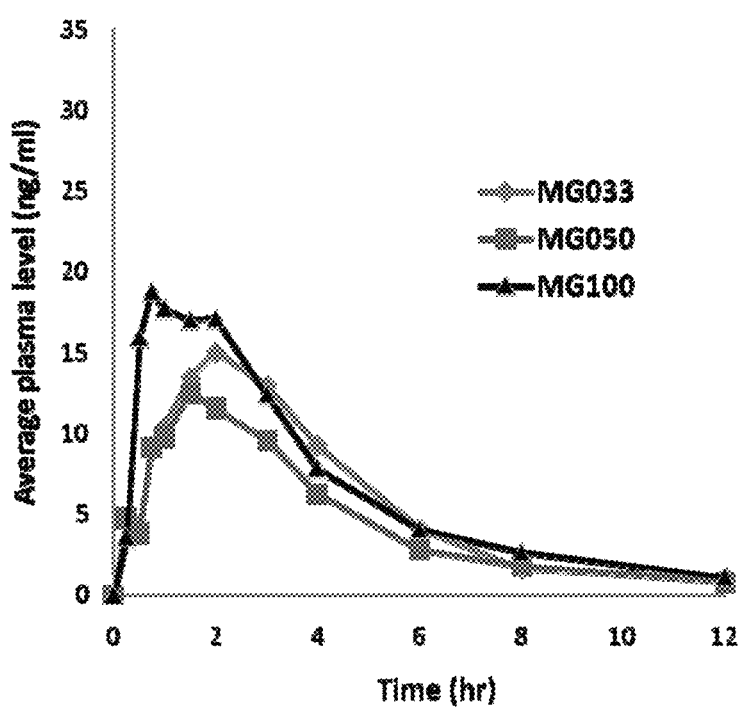
FIG. 1 graphs the plasma levels versus time after administration resulting from three liquid dosage forms not containing absorption enhancers with different dosage amounts of rizatriptan.

In accordance with this invention, a new delivery matrix is provided for administering pharmaceutically active agents (also known as active compounds) to a patient by means of selective absorption through mucous membranes located in the mouth. Absorption is the movement of drug into the blood stream. This invention constitutes a matrix which can be incorporated into new oral dosage forms such as a film or tablet and a liquid dosage form. The term oral dosage form shall include but not be limited to an oral disintegrating tablet, paste, gel, liquid, emulsion, film, lollipop, lozenge, buccal and gingival patch, granule and powdered dosage forms. The terms dosage form or dosage unit shall mean the combination of the matrix, which comprises a pharmaceutical active agent and one or more fatty acid esters of sucrose having a combined HLB of about 8 to about 16, preferably about 9 to about 16, with additional ingredients to form a tablet, paste, gel, liquid, emulsion, film, lollipop, lozenge, buccal and gingival patch, granule and powdered dosage form for insertion into the mouth of a patient. The dosage forms are preferably water soluble. The dosage form contains an effective amount of the pharmaceutically active agent distributed therein. The dosage form may optionally contain a polymeric mixture of polyvinyl pyrrolidone and a polymeric alginate. When the dosage form is a solid it may be contoured to a size suitable for insertion into the mouth. Preferred solid dosage forms are a film (ODF) and a tablet (ODT). Insertion into the mouth preferably occurs by sublingual or buccal insertion which allows the pharmaceutical agent to be delivered to the patient selectively through the mucosa in the mouth thereby bypassing the GI system and allowing effective administration of pharmaceutical active agents that generally cause GI irritation or are rendered inactive in the GI system. Anti-migraine agents in the chemical class triptans are known to cause GI irritation and are also known to be rendered at least partially inactive by GI exposure. In some instances, the dosage form is placed on to the tongue where absorption may also take place. The dosage forms of this invention act as a carrier device to transmit the pharmaceutically active agents to a patient in a fast and effective manner. Preferably, the liquid dosage form will be placed under the tongue for sublingual absorption.

When only pharmaceutically active agent and fatty acid ester of sucrose are present in the liquid, then the matrix is the dosage form.

This invention also is directed to a process for mitigating migraine headaches, cluster headaches and related symptoms of migraine and cluster headaches in a patient by administering the oral unit dosage form into the mouth of the patient. Typical migraine symptoms are painful headaches that can be one-sided and pulsating, lasting 4 to 72 hours. Accompanying complaints are nausea and vomiting, and a heightened sensitivity to bright lights (photophobia) and noise (hyperacusis). Approximately one third of people who experience migraines get a preceding aura, in which a patient may sense a strange light or unpleasant smell.

In one embodiment, of the present invention, the pharmaceutically active agent is an anti-migraine agent. The preferred anti-migraine agents are triptans selected from the group consisting of eletriptan, frovatriptan, sumatriptan, zolmitriptan, naratriptan, rizatriptan and almotriptan or pharmaceutically acceptable salts thereof. Suitable pharmaceutically acceptable salts of the active agents used in the dosage forms of this invention include acid addition salts which may, for example, be formed by mixing a solution of the pharmaceutically active agent according to the invention with a solution of a pharmaceutically acceptable non-toxic acid such as hydrochloric acid, fumaric acid, maleic acid, succinic acid, acetic acid, benzoic acid, oxalic acid, citric acid, tartaric acid, carbonic acid or phosphoric acid. These anti-migraine agents are present in the dosage form in an amount effective for combating migraine by either treating the migraine headache and related symptoms or preventing the onset of the migraine headache and related symptoms. By insertion of this dosage form into the mouth of the patient, the pharmaceutical agent is delivered by selective absorption through the patient's oral mucosa tissue. In another embodiment of the present invention, the dosage form is placed on the tongue. In another embodiment of the present invention, a liquid matrix is placed in the mouth of the patient and held there until the active agent has been absorbed. Absorption may take from about 0.5 minute to about 15 minutes preferably about 1 minute to about 10 minutes and more preferably 1 minute to about 5 minutes. Placing the liquid dosage form into the patient's mouth under the tongue is preferred. Liquid dosage forms may be applied by spraying into the mouth from suitable spray device or placed into the mouth with an eye dropper, pipette or similar device. Applicators are well known in the art. Dosing by film, tablet or liquid is preferably once or twice daily. Dosing may vary according to the age of the patient, severity of the condition and the particular active agent.

When the pharmaceutical agent is a triptan, the triptan is present in the dosage form in the amount of from about 1 mg to about 100 mg as the base. When the pharmaceutical agent is almotriptan it is present in an amount of about 2.5 to about 15 mg as the base. When the pharmaceutical agent is rizatriptan it is present in an amount of about 2.5 to about 15 mg as the base. When the pharmaceutical agent is naratriptan it is present in an amount of about 1 to about 5 mg as the base. When the pharmaceutical agent is zolmitriptan it is present in an amount of about 1 to about 7.5 mg as the base. When the pharmaceutical agent is sumatriptan it is present in an amount of about 3 to about 100 mg as the base. Preferably, sumatriptan is present from about 3 to about 50 mg as the base and more preferably from about 3 to about 25 mg as the base. When the pharmaceutical agent is frovatriptan it is present in an amount of about 1 to about 5 mg as the base. When the pharmaceutical agent is eletriptan it is present in an amount of about 10 to about 30 mg as the base.

The term "triptan" as used herein includes compounds designed around an indole ring, with neurotropic activity in suppression of migraine pain. These include the free base form of this compound and its salts of this compound as well as all pharmacologically acceptable analogs, derivatives, and chemically modified forms, including acid addition salts, thereof. In addition to chloride, other acceptable salts are the bromide, the iodide, the sulfuric, the phosphate, the acid phosphate, the lactate, the citrate, the tartarate, the salicylate, the succinate, the maleate, the gluconate, mesylate, and the like. Also included are fatty acid salts of the form "lipophilic ion pairs", such as the laurate, dodecylate, myristate, palmitate, stearate, coconoate, behinate, oleate, linoleate, linolenate, eicosapentaenoate, eicosahexaenoate, docosapentaenoate, docosahexaenoate, and eicosanoids in general. Additional suitable pharmaceutically acceptable salts of the compounds of this invention include acid addition salts which may, for example, be formed by mixing a solution of the compound according to the invention with a solution of a pharmaceutically acceptable non-toxic acid such as hydrochloric acid, fumaric acid, acetic acid, benzoic acid, oxalic acid, carbonic acid or phosphoric acid. Preferred pharmaceutically acceptable salts of rizatriptan are oxalate, succinate, hydrochloride and benzoate salts. In the treatment of migraine, a suitable dosage level for the rizatriptan or its pharmaceutically acceptable salts is from about 0.05 to 5 mg per kg as the base per day. In general with respect to rizatriptan, the film which forms the unit dosage form contains an amount of rizatriptan or its pharmaceutically acceptable salts, with amounts of from about 1 mg to about 25 mg as the base with about 2 mg to about 20 mg as the base being preferred and about 2.5 to about 15 mg as the base being most preferred. Generally this unit dose will vary depending upon the size and weight of the patient and the amount desired by the physician to be effective for treating and/or preventing the onset of migraine headaches.

In a preferred embodiment of the present invention the dosage form is a water soluble film comprising the matrix and a polymeric mixture of polyvinyl pyrrolidone and a polymeric alginate. Preferably the film contains from about 5% to about 95% by weight of polyvinyl pyrrolidone and from about 5% to about 95% of the polymeric alginate, both weights being based upon the weight of the film. This film is formed from an aqueous mixture containing from about 5% to about 95% by weight of polyvinyl pyrrolidone and from about 5% to about 95% of the alginate salt, both weights being based upon the dry weight of the mixture. The alginate salt can be any conventional pharmaceutically acceptable salt, preferably the alkali earth metal salts and more preferably sodium alginate. Both the polyvinyl pyrrolidone and a polymeric alginate utilized in forming this film are water soluble. Sufficient water is used in the formation of the aqueous mixture to dissolve the polyvinyl pyrrolidone and alginate salt.

The polyvinyl pyrrolidone which is utilized in forming the film has a molecular weight of from about $1\times10^3$ to about $1\times10^8$ daltons and the polymeric alginate has a molecular weight of from about $1\times10^3$ to about $1\times10^7$ daltons and a viscosity of from about 400 cps to about 900 cps measured in a 1% by weight aqueous solution.

In a preferred embodiment of the present invention the dosage form is a water soluble film comprising the matrix and pullulan. Pullulan typically has a molecular weight of about 5,000 to about 5,000,000 daltons and preferably pullulan has a molecular weight of about 10,000 to about 800,000 daltons.

The film oral solid dosage unit has a surface area of from about 0.25 cm² to about 20 cm² and a weight of about 1 mg to about 200 mg, preferably from about 1 cm² to about 10 cm² and a weight of about 10 mg to about 500 mg, preferably about 10 mg to about 250 mg. The dry film has a thickness of between about 0.01 mm to about 5 mm, preferably between about 0.05 mm to about 2.5 mm. The film will dissolve in the oral cavity in about 0.25 minutes to about 15 minutes, preferably in about 0.5 minutes to about 10 minutes. When the pharmaceutical composition is a the tablet, when the placed in the oral cavity it will dissolve in about 0.25 minutes to about 15 minutes.

When the pharmaceutical composition is a film and said film preferably contains one or more absorption enhancers in an amount of from about 0.1% by weight to about 15% by weight of the film, more preferable, said film contains a absorption enhancer in an amount of from about 1% by weight to about 10% by weight of the film.

When the pharmaceutical composition is a tablet said tablet preferably contains a absorption enhancer in an amount of from about 0.1% by weight to about 20% by weight of the tablet, more preferably said tablet contains a absorption enhancer in an amount of from about 1% by weight to about 15% by weight of the tablet.

When the pharmaceutical composition is a liquid contains a absorption enhancer in an amount of from about 0.1% by weight to about 10% by weight of the liquid.

In controlled release oral solid dosage forms, films or tablets, the ratio of polyvinyl pyrrolidone to polymeric alginate in the polymeric mixture is from about 5:1 to about 1:3. By selecting different ratios of polyvinyl pyrrolidone to polymeric alginate, the dissolution time of the film may be controlled. The reported dissolution data illustrating the effect of the ratio of PVP to polymeric alginate for films are tabulated in Table 1. Each dissolution time represents the average of six determinations. The subjects placed the film into their mouths either buccal or sublingual and the time to total dissolution was measured.

TABLE 1

Film Characteristics - Dissolution

| Sample Code | A | B | C | D | E |
|---|---|---|---|---|---|
| Ratio of PVP/alginate | 5:1 | 4:1 | 3:1 | 1:2 | 1:3 |
| Average dissolving time (buccal, 2.5 cm²) | 4 min | 6 min | 9 min | 17 min | 26 min |
| Average dissolving time (sublingual, 5 cm²) | 3.5 min | 4.5 min | 7 min | 14 min | 17 min |

The procedure for preparing the films of table 1 is described in Examples 1 and 2. The ratio of PVP to polymeric alginate was adjusted by the techniques illustrated in Examples 2, 2A, 2B, 3 to 9. In forming the film, the polyvinyl pyrrolidone and the polymeric alginate salt are mixed in an aqueous solution and the other materials, including the pharmaceutically active agent and absorption enhancers, used in forming the dosage form of this invention are mixed into this solution.

The greater molecular weight of the polyvinyl pyrrolidone the greater will be the drug release time of the films so produced. This is illustrated in Table 3 and Examples 7 and 8. Example 7 contains a PVP:alginate ratio of 2:1 and 0.1620 grams of PVP K60 with a molecular weight of 337,000 daltons. Example 8 contains a PVP:alginate ratio of 2:1 and 0.1620 grams of PVP K30 with a molecular weight of 44,000 to 54,000 daltons. Example 7 has a buccal release time of ii minutes 15 seconds and a sublingual release time of 9 minutes 53 seconds. Example 8 has a buccal release time of 8 minutes 44 seconds and a sublingual release time of 6 minutes 34 seconds. The molecular weights of PVP K60 of 337,000 daltons compared to the molecular weight of PVP K30 of 44,000 to 54,000 daltons being the only difference between the two formulations.

In fact, as the ratio of polymeric alginate to polyvinyl pyrrolidone in the polymeric mixture is increased the release time from the film that is formed will also increase. By varying the molecular weight of polyvinyl pyrrolidone and the ratio of the polyvinyl pyrrolidone to the polymeric alginate one can obtain a release time of from about 1 minute to about 1 hour or longer.

Additional polymers may be incorporated into the matrix as release controlling additives. Suitable additional polymers may be selected from the group comprising hydroxy propyl methyl cellulose, hydroxy ethyl cellulose, hydroxy propyl cellulose and polyethylene glycol and like polymers. Preferably, hydroxy ethylcellulose can be used to decrease film hydrophilicity and increase dissolution time to over 25 minutes for both buccal and sublingual applications. Hydroxy propyl methylcellulose can be also included to decrease film hydrophilicity and at the same time to decrease dissolution time to the range of 1-5 minutes. Formulations illustrating the release controlling effect of additional polymers are found in Examples 9 to 13.

The unit dosage form may contain known pharmaceutically acceptable additives, flavoring agents, surfactants and adjuvants. Conventional plasticizers such as glycerol may also be present in amounts up to about 40%. Specifically examples of release-controlling additives such as hydroxypropyl methylcellulose, hydroxypropyl cellulose, and hydroxy ethyl cellulose can be added. Conventional flavors such as peppermint oil, sugar or other natural and artificial sweeteners and natural and artificial flavors may be present in the same form of composition of this invention. These additives, flavoring agents, sweeteners, plasticizers, surfactants and adjuvants may be incorporated into the film by adding to or mixing them into the aqueous solution which is used to form the film. Generally it is desired that these agents are present in the amount of from about 0.1% to about 20%. The controlled release matrix may contains one or more absorption enhancers present in an amount of from about 0.1% to about 20% based upon the weight of the dosage unit which may be a film or tablet preferably from about 1% to about 20%.

When the unit dosage form further comprising a nonionic surfactant, the combined nonionic surfactant and sucrose fatty acid ester have a combined HLB of about 8 to about 17.

The solid oral unit dosage form of this invention can be utilized to transport any desired water soluble pharmaceutically active agent. As used herein, the term "effective amount" designates the amount of drug or pharmaceutical agent that produces the desired biological or medical response of a patient. In accordance with this invention depending upon the pharmaceutical agent that is administered and the desired biological or medical response of a patient desired by the physician, the effective amount will vary. In general, the amount of a pharmaceutically active agent conventionally administered in other unit dosage forms can be used and administered by the unit dosage form of this invention. The dose of pharmaceutically active agent may be adjusted to take into account differences in absorption due to the different route of administration. The term "selective" as used herein is means that a major portion of the pharmaceutical agent administered passes through the mucosal membranes of the mouth rather than through the gastrointestinal tract.

The preferred pharmaceutical agent for use in the oral unit dosage form of this invention is an agent for treatment or prevention of migraine headaches in a patient. The amount which is presented in the dosage form of this invention should be that amount which is effective for treating or preventing a migraine headache. Any conventional water soluble pharmaceutical agent for use for treatment or prevention of migraine headaches can be used in the amounts that they are conventionally used in other oral dosage forms. The preferred migraine agents for use in the oral unit dosage form of this invention are triptans and their pharmaceutically acceptable salts and rizatriptan, sumatriptan, zolmitriptan or their pharmaceutically acceptable salts are preferred. These preferred agents are known agents for use in combating migraine headaches. The specially preferred agent is rizatriptan or its pharmaceutically acceptable salts, most preferable the benzoate salt.

The unit oral dosage of this invention contains a pharmaceutically acceptable mucosal penetrating or permeation enhancer. These pharmaceutically acceptable mucosal penetrating or permeation enhancers are incorporated into the film or tablet by adding to or mixing them into the solution which is used to form the film or tablet. These pharmaceutically acceptable mucosal penetrating or permeation enhancers are present in the total amount of about 0.5% to about 20%, preferably about 1% to about 20%, more preferably about 1% to about 10% and most preferably about 2% to about 10% based upon the weight of the dosage form. The preferred pharmaceutically acceptable mucosal penetrating or permeation enhancers are selected from the esters of sucrose particularly the $C_{12}$ to $C_{20}$ saturated fatty acid esters of sucrose. When one or more than one fatty acid ester of sucrose is included in the matrix, that is a film, oral disintegrating tablet, liquid, spray, paste, gel, oral film, lollipop, lozenge, buccal and gingival patch, the combined HLB of the fatty acid esters of sucrose will have an HLB of about 8 to about 16; preferably about 9 to about 16 and most preferably about 9.5 to about 16. The preferred fatty acid esters of sucrose are selected from the group consisting of sucrose stearate, sucrose palmitate, sucrose laurate, sucrose behenate, sucrose oleate and sucrose erucate. Table 2 lists the HLB values for fatty acid esters of sucrose and the monoester content.

TABLE 2

HLB Value of Fatty Acid Esters of Sucrose

| ESTER | Trade Name | HLB value | Mono ester content |
|---|---|---|---|
| Sucrose stearate | S-070 | <1 | <1% |
| | S-170 | 1 | 1% |
| | S-270 | 2 | 10% |
| | S-370 | 3 | 20% |
| | S-370 Fine | 3 | 20% |
| | S-570 | 5 | 30% |
| | S-770 | 7 | 40% |
| | S-970 D-1809 | 9 | 50% |
| | S-1170, D-1811 | 11 | 55% |
| | S-1570 D-1815 | 15 | 70% |
| | S-1670 D-1816 | 16 | 75% |

TABLE 2-continued

HLB Value of Fatty Acid Esters of Sucrose

| ESTER | Trade Name | HLB value | Mono ester content |
|---|---|---|---|
| Sucrose palmitate | p-170 | 1 | 1% |
| | P-1570 D-1615 | 15 | 70% |
| | P-1670 D-1616 | 16 | 80% |
| Sucrose laurate | L-195 | 1 | 1% |
| | L-595 | 5 | 30% |
| | LWA-1570 | 15 | 70% |
| | L-1695 D-1216 | 16 | 80% |
| Sucrose behenate | B-370 | 3 | 20% |
| Sucrose oleate | O-170 | 1 | 1% |
| | OWA-1570 | 15 | 70% |
| Sucrose erucate | ER-190 | 1 | 0% |
| | ER-290 | 2 | 2% |
| Sucrose ester of mixed fatty acids | POS-135 | 1 | 0% |

The hydrophilic-lipophilic balance (HLB) of a surfactant is a measure of the degree to which it is hydrophilic or lipophilic, determined by calculating values for the different regions of the molecule, as described by W. C. Griffin "Classification of Surface-Active Agents by 'HLB,'" Journal of the Society of Cosmetic Chemists 1 (1949): 311. and W. C. Griffin "Calculation of HLB Values of Non-Ionic Surfactants," Journal of the Society of Cosmetic Chemists 5 (1954): 259. Other methods have been suggested, notably by J. T. Davies "A quantitative kinetic theory of emulsion type, I. Physical chemistry of the emulsifying agent," Gas/Liquid and Liquid/Liquid Interface. Proceedings of the International Congress of Surface Activity (1957): 426-438. All three references are incorporated herein by reference.

The HLB for a combination of components with differing HLB value is by the following formula:

$$HLB \text{ for a combination of components} = \frac{\sum_{i=1}^{n}(H_i \times A_i)}{\sum_{i=1}^{n}(A_i)}$$

where $H_i$ is the HLB value of individual component and $A_i$ is the amount of individual component.

The matrix of a preferred embodiment may further comprise a nonionic surfactant. Preferred nonionic surfactants may be one or more of a polysorbate and sorbitan fatty acid ester.

The polysorbate useful in the present invention is selected from the group consisting of polyoxyethylene (20) sorbitan monolaurate, polyoxyethylene (20) sorbitan monopalmitate, polyoxyethylene (20) sorbitan and polyoxyethylene (20) sorbitan monooleate.

The sorbitan fatty acid ester useful in the present invention is selected from the group consisting of sorbitan monolaurate, sorbitan monopalmitate, sorbitan monostearate, sorbitan tristearate and sorbitan monooleate.

The matrix of this invention may further comprise a secondary absorption enhancer selected from the group consisting of glycerol, ginger oil, cineole and terpenes. Preferred terpines include limonene, cymene, pinene, pellandrene and the like.

The oral unit dosage form of this invention is produced by forming an aqueous solution of the matrix and polyvinyl pyrrolidone and the polymeric alginate. In preparing the film, the aqueous solution containing polyvinyl pyrrolidone and sodium alginate is mixed with pharmaceutically active ingredient, plasticizers and pharmaceutically acceptable additives, flavoring agents, adjuvants. This mixture is then cast into films by coating and drying generally using a coating and casting machine. Any conventional means of casting the films by means of these machines can be utilized in carrying out the procedure for forming the films. The aqueous mixture containing the polyvinyl pyrrolidone, sodium alginate, pharmaceutically active ingredient, plasticizers as well as certain desirable pharmaceutically acceptable additives, flavoring agents, adjuvants is coated on a release liner such as a polyester film. Any conventional release liner can be utilized for this purpose. Generally the release liner has a silicone surface to facilitate release of the film after drying. After the aqueous solution containing the polymeric mixture of polyvinyl pyrrolidone and alginate polymer is coated on the surface of the release liner, the coated release liner is heated to a temperature to dry the coated solution and allow the polyvinyl pyrrolidone and the alginate form a polymeric film with the pharmaceutically active agent dispersed therein, preferably uniformly dispersed therein. Generally drying can take place at from about 60° to 80° C. or higher depending on thickness of the film desired. Drying time can range from 10 minutes for 4 hours. The drying and formation of polyvinyl pyrrolidone and sodium alginate polymer films can be carried out by conventional means. Once the film is dried, the film is die-cut into standard sizes and removed from the release liner to produce the oral unit dosage form. Generally for the oral usage dosage in the form of the film has a surface area from about 0.25 cm$^2$ to about 20 cm$^2$ and a weight of about 1 mg to about 200 mg, preferably from about 1 cm$^2$ to about 10 cm$^2$ and a weight of about 10 mg to about 200 mg and a thickness of from about 0.1 mm to about 5 mm.

In preparing the orally disintegrating tablet, the fatty acid ester of sucrose is dissolved in a solvent such as isopropyl alcohol at elevated temperature of about 60° C. Certain adjuvants such as flavoring agents, and nonionic surfactants are added to the solution to form solution A. If to be included in the tablet release controlling agents such as polyvinyl pyrrolidone (PVP) and alginate salt is prepared by dissolving in water. Fillers and sweeteners such as mannitol and sucrose are blended to become a powder B. In a fluidized-bed granulator, powder B is sprayed with solution A and the optional PVP:alginate solution. The mixture is dried until completely dry. The mixture is then passed through a 20 mesh screen or similar process to produce a granulation. This granulated PVP is combined with pharmaceutically active agent, preferably a triptan and additional dry ingredients such as the additional polymers, sweetener, lubricant which have a particle size equivalent to being passed through a 60 mesh screen to form the final granulation for tableting. Tablets of appropriate size and shape are then prepared by techniques well know in the pharmaceutical arts. The formation of tablets that rapidly dissolve in the oral cavity is known in the art. Such tablets have, for example, been described in U.S. Pat. Nos. 7,431,942; 5,464,632; and 5,026,560 which are incorporated herein by reference.

Liquid dosage forms are prepared by dissolving the active agent and absorption enhancer in water. This liquid dosage form contains an effective amount of the pharmaceutically active agent dissolved therein. This liquid dosage form further comprises one or more fatty acid esters of sucrose as absorption enhancer having a combined HLB of about 8 to about 16; preferably about 9 to about 16 and more preferably about 9.5 to about 16. Conventional flavorants such as peppermint oil, natural and artificial flavorants, sugar or other natural and artificial sweeteners may be present in the same form of composition of this invention. These additives, flavoring agents, plasticizers and adjuvants may be incorporated into the liquid dosage form by adding to or mixing them into the aqueous solution. Small amounts of alcohol may be helpful in achieving solution of these components. Generally it is desired that these agents are present in the amount of from about 0.1% to about 20%. Flavorant is defined as a substance that gives another substance flavor, altering the characteristics of the solute, causing it to become sweet, sour, tangy, etc. There are three principal types of flavorings used in foods and useful in this invention, under definitions agreed in the E.U. and Australia:

Natural Flavouring Substances:

Flavouring substances obtained from plant or animal raw materials, by physical, microbiological or enzymatic processes. They can be either used in their natural state or processed for human consumption, but cannot contain any nature-identical or artificial flavouring substances.

Nature-Identical Flavouring Substances:

Flavouring substances that are obtained by synthesis or isolated through chemical processes, which are chemically identical to flavouring substances naturally present in products intended for human consumption. They cannot contain any artificial flavouring substances.

Artificial Flavouring Substances:

Flavouring substances not identified in a natural product intended for human consumption, whether or not the product is processed.

Other active agents or medicaments that would benefit from absorption in the oral cavity, in particular sublingual administration, may be included in the present invention. By the terms "active agent" the present invention refers to a compound that has a desired therapeutic or physiological effect once ingested and/or metabolized. The therapeutic effect may be one which provides the physical relief from a malady (e.g., diminishes pain, acid reflux or other discomfort), has an effect on the brain chemistry of molecules that determine mood and behavior. Of course these are just examples of what is intended by therapeutic effect. Those of skill in the art will readily recognize that a particular agent has or is associated with a given therapeutic effect.

The active agent may be any agent that is traditionally used as a medicament and lends itself to being administered through the oral cavity. Such active agents may be vitamins, chemotherapeutics; antimycotics; oral contraceptives, nicotine or nicotine replacement agents, analgesics, muscle relaxants, antihistamines, decongestants, anesthetics, antitussives, diuretics, anti-inflammatories, antibiotics, antivirals, psychotherapeutic agents, anti-diabetic agents, sexual dysfunction agents and cardiovascular agents.

The following classes of drugs and non-limiting examples and their corresponding salts are applicable for delivery using an orally dissolving film, particular those which can benefit from a fast onset time or have a low oral bioavailability including:

Smoking cessation drugs:
Nicotine, nicotine polacrilex, nicotine bitartrate, hydrochloride and nicotine citrate, nicotine maleate or mixtures thereof other salts nicotine replacement agents Narcotic analgesics:
    Fentanyl, hydromorphone, morphine, sufentanyl, methadone, buprenorphine
Anesthetic:
    Lidocaine (xylocaine), provacaine, benzocaine,
Antitussives (OTC handbook for cough, cold, asthma):
    Hexylrescinol, dextromorphine,
Nonnarcotic analgesics such as the nonsteroidal anti-inflammatory agents (NSAIDS):
    Acetaminophen, Ibuprofen, ketoprofen, indomethacin, aspirin (low dose for cardiovascular), naproxen sodium, ketorolac, diclofenac, meloxicam, peroxicam,
Erectile dysfunction:
    Sildenafil, tadafil, vardenafil
Female sexual dysfunction
    Sildenafil, tadifil, vardenafil
Antihistamines: Colds and Allergy:
    Certrizine HCl, loratadine, chlorcyclizine HCl, Chlorpheniramine maleate, dextrochlorpheniramine maleate, dexbrompheniramine mealate, diphenhydramine citrate, diphenhydramine HCl, doxylamine succinate, phenindamine tartrate, pheniramine, pyrilamine mealate, triprolidine HCl, thonzylamine HCl, clemastine fumarate,
Cough:
    Menthol, camphor, dextromethorphan HBr, guaifenesin, codeine phosphate, codeine
Respiratory Disorders
    Pseudoephedrine HCl, phenylephrine HCl, guaifenesin, dextromethorphan HBr.
Sore Throat:
    Benzocaine, menthol, dyclonine, phenol
Respiratory Disorders:
    Ephedrine
Heartburn and Dyspepsia:
    Cimetidine, nizatidine, famotidine, ranitidine, omeprazole
Antiemetics:
    Granisetron, ondansetron, etc. AZ-001, AZ-004, Levadex, Zelrix, VR-147, ROX-828, COL-144, BF-1, diphenhydramine, scopolamine, and the like
Sleep aids:
    Zolpidem, Eszopiclone (Lunesta), Zalepon (Sonata), diphenhydramine, doxylamine, benzodiazepines (such as: Estazolam (ProSom), Flurazepam (Dalmane), Temazepam (Restoril), Triazolam (Halcion), Ramelteon (Rozerem)
Diarrhea:
    Loperamide, digestive enzymes (lactase) bismuth subsalicylate
Oral Hygiene:
    Cetylpyridinum chloride, domiphen, thymol, eucalyptol, methyl salicylate, menthol, stannous fluoride, sodium fluoride, benzocaine, phenol, docosanol
Antagonists of CGRP receptors as described in U.S. Pat. No. 7,534,784 incorporated in its entirety herein by reference.
Migraine treatment: triptans/CGRP
    Rizatriptan, zomitriptan,
    Telcagepant, BIBN4096 (Olcegepant)
Other drugs where a convenience of dosing without the need for liquids to enhance compliance can benefit from delivery in an orally dissolving film such as:

Drugs for hormone replacement
    Estradiol, testosterone
Alzheimer's disease: cholinergics/cholinesterase inhibitors
    Donezapil, galantamine, rivastigmine, tacrin, memantine, etc. and their salts
    Caffeine salt compounds such as caffeine citrate, caffeine sodium benzoate, caffeine sodium salicylate, which may be more water soluble and less bitter than caffeine, may also benefit from delivery in an orally dissolving film or ODT of the present invention.

The following examples describe embodiments of the present invention is more detail.

In the Examples, the following are definition of the ingredients used.

Polyvinyl pyrrolidone (PVP) K90: M.W.=1000000-1500000
    K60: M.W.=337000
    K30: M.W.=44,000-54,000
The average molecular weight of soluble polyvinylpyrrolidone (PVP) is expressed in terms of K-value in the pharmacopoeias valid in Europe, Japan and USA. It is calculated from the relative viscosity in water and always forms a part of the commercial name.
Kelvis: Sodium alginate with high viscosity (760 CPS @ 1% solution), M.W=134,640
Methocel K100 (LV): Hydroxypropyl methylcellulose, MW=26000
Methocel E4M: Hydroxypropyl methycellulose, MW=93000
Natrosol 250H Hydroxyethylcellulose (HEC) is a high viscosity grade (1% solution, 1500-2500 cps).
Manugel LSA: Sodium alginate with low viscosity (10% solution, 500 cps), M.W=15840
Polyox WSR 205: High MW (M.W.=600,000) Water Soluble Resin Polyethylene Glycol Example 1

Base Solution Preparation

To simplify the mixing operation, "base solution" was prepared by mixing 20 grams isopropanol, as solubilizer, and 64 grams glycerol, as plasticizer, followed by the addition of 6.4 grams of sucrose ester (HLB 11), 2.4 grams sucrose ester (HLB 5), 4 gram Tween 80 and 0.8 grams Span 80, as permeation enhancers. The mixture was heated gently to 45-50° C. with mixing. While the solution was still warm, 0.2 gram of ginger oil and 0.08 gram of peppermint oil, as flavors, were added and mixed until uniform. Upon cooling to room temperature, a white opaque paste would form.

Example 2

PVP/Alginate Film 3:1

0.90 grams of 20% polyvinylpyrrolidone (PVP K90, M.W.=1.0-1.5×10$^6$) in water, and 3.0 grams of 2.0% high viscosity sodium alginate (Kelvis, viscosity=760 cps @ 1% solution) in water were mixed until the solution was uniform. With mixing these, 0.245 grams of above "base solution", 0.0513 gram rizatriptan benzoate (14.53 mg of Rizatriptan benzoate is equivalent to 10 mg rizatriptan base), and 0.025 gram of aspartame, as taste-masking agent, were added. Ensure minimal air entrapment in the solution during mixing. The final viscous mixture was then degassed in a vacuum chamber until it was air bubble free. This viscous mixture was now ready for wet casting into films on the coating/drying machine. The film fabrication procedure is described below.

The film coating/drying machine (Werner Mathis AG) was used to cast the films. Depending on formula, the machine was first heated to a specific temperature ranging between 40°-80° C. or higher if needed. The wet film thickness, the gap setting between the doctor knife and the top of release liner surface, was set at 1 mm for buccal application and at 2 mm for sublingual application as adjusted by the micrometer dial. The degassed viscous mixture was poured from the solution container across the cross section of the stretched release liner that was pulled tightly to form a smooth flat surface. When ready to coat, the knife was drawn slowly over the coating solution which would spread the solution evenly to form a uniform thickness film. The casted wet film on the release liner was immediately entered into the drying compartment of the machine set at 800° C. Depending on dry film thickness and its application, the 0.1 mm film for buccal application, drying time at 80° C. was about 20 minutes. The 0.2 mm thickness film for sublingual application, drying time would be double or around 40 minutes.

The dried films were then die-cut into 5 cm² size with both 0.1 and 0.2 mm thickness. The targeted 0.1 mm film each 5 cm² would weigh around 50 mg with 5 mg rizatriptan benzoate. The targeted 0.2 mm film, the same 5 cm² would weigh 100 mg and contain 10 mg rizatriptan benzoate.

Example 2A

PVP/Alginate Film 4:1

1.20 grams of 20% polyvinylpyrrolidone (PVP K90, M.W.=1.0-1.5×10$^6$) in water, and 3.0 grams of 2.0% high viscosity sodium alginate (Kelvis, viscosity=760 cps @ 1% solution) in water were mixed until the solution was uniform. With mixing these, 0.245 grams of above "base solution", 0.0513 gram rizatriptan benzoate (14.53 mg of rizatriptan benzoate is equivalent to 10 mg rizatriptan base), and 0.025 gram of aspartame, as taste-masking agent, were added. Ensure minimal air entrapment in the solution during mixing. The final viscous mixture was then degassed in a vacuum chamber until it was air bubble free. This viscous mixture was now ready for wet casting into films on the coating/drying machine. The film fabrication procedure was as described above.

The targeted 0.1 mm film each 5 cm² would weigh around 50 mg with 5 mg rizatriptan benzoate. The targeted 0.2 mm film, the same 5 cm² would weigh 100 mg and contain 10 mg rizatriptan benzoate.

Example 2B

PVP/Alginate Film 5:1

1.50 grams of 20% polyvinylpyrrolidone (PVP K90, M.W.=1.0-1.5×10$^6$) in water, and 3.0 grams of 2.0% high viscosity sodium alginate (Kelvis, viscosity=760 cps @ 1% solution) in water were mixed until the solution was uniform. With mixing these, 0.245 grams of above "base solution", 0.0513 gram rizatriptan benzoate (14.53 mg of rizatriptan benzoate is equivalent to 10 mg rizatriptan base), and 0.025 gram of aspartame, as taste-masking agent, were added. Ensure minimal air entrapment in the solution during mixing. The final viscous mixture was then degassed in a vacuum chamber until it was air bubble free. This viscous mixture was now ready for wet casting into films on the coating/drying machine. The film fabrication procedure is as described above.

The dried films were then die-cut into 5 cm² size with both 0.1 and 0.2 mm thickness. The targeted 0.1 mm film each 5 cm² would weigh around 50 mg with 5 mg rizatriptan benzoate. The targeted 0.2 mm film, the same 5 cm² would weigh 100 mg and contain 10 mg rizatriptan benzoate.

Example 3

PVP/Alginate Film 2:1

0.80 grams of 20% PVP K90 in water and 4.0 grams of 2.0% Kelvis in water were mixed together. While still mixing, 0.245 gram of the "base solution", 0.0513 gram rizatriptan benzoate and 0.025 grams of aspartame were added. The resulting viscous mixture was then degassed in a vacuum chamber until it was air bubble free for use in film casting. The film fabrication procedure was the same as above Example 2.

Example 4

PVP/Alginate Film 1:1

0.60 grams 20% PVP K90 in water and 6.0 grams of 2.0% Kelvis in water were first mixed together and then with 0.245 gram of "base solution", 0.0513 gram rizatriptan benzoate and 0.025 grams of aspartame. The mixture was mixed until uniform and degassed in a vacuum chamber until it was bubble free for film casting. The film fabrication procedure was the same as above Example 2.

Example 5

PVP/Alginate Film 1:2

0.40 grams 20% PVP K90 in water and 8.0 grams of 2.0% Kelvis in water were first mixed together and then with 0.2450 gram of "base solution", 0.0513 gram rizatriptan benzoate and 0.0250 grams of aspartame. The mixture was mixed until uniform and degassed in a vacuum chamber until it was bubble free for film casting. The film fabrication procedure was the same as above Example 2.

Example 6

PVP/Alginate Film 1:3

0.30 gram of 20% PVP K90 in water and 9.0 grams of 2% Kelvis in water were first mixed together and then with 0.245 gram "base solution", 0.0513 gram rizatriptan benzoate and 0.025 grams of aspartame. The degassed mixture was then used for film casting. The film fabrication procedure was the same as above Example 2.

Example 7

PVP K60/Alginate Film 2:1

0.46 gram of 35% PVP K60 (MW=337,000) in water and 1.0 grams of 8% low viscosity sodium alginate (Manugel LBA) in water were first mixed together. This was followed by the addition of 0.245 gram "base solution", 0.0513 gram rizatriptan benzoate and 0.025 grams of aspartame. The degassed mixture was then used for film casting. The film fabrication procedure was the same as above Example 2.

Example 8

PVP K30/Alginate Film 2:1

0.27 gram of 60% PVP K30 (MW=44,000-54,000) in water and 1.0 grams of 8% Manugel LBA in water were first mixed together. This was followed by the addition of 0.245 gram "base solution", 0.0513 gram rizatriptan benzoate and 0.025 grams of aspartame. The degassed mixture was then used for film casting. The film fabrication procedure was the same as above Example 2.

Example 9

PVP/Alginate & HEC Film 1:1

0.60 gram of 20% PVP K90 in water, 0.75 grams of 8% Manugel LBA in water, and 3.0 grams of 2% high viscosity hydroxyethylcellulose (Natrosol 250H) in water were first mixing together until it formed a uniform solution. This was followed by the addition with mixing 0.245 gram "base solution", 0.0513 gram rizatriptan benzoate and 0.025 grams of aspartame. The degassed mixture was then used for film casting. The film fabrication procedure was the same as above Example 2.

Example 10

High MW PEG/Alginate & HEC Film 2.0 grams of 4% polyethylene glycol (Polyox WSR 205, MW=600000) in water, 2.7 grams of 2% Natrosol 250H in water and 1.35 grams of 8% Manugel LBA in water were mixed with 0.245 gram "base solution", 0.0513 gram rizatriptan benzoate and 0.025 gram of aspartame. The degassed mixture was then used for film casting. The film fabrication procedure was the same as above Example 2.

Example 11

HPMC/PVP/Alginate Film 1.66 gram of 6% hydroxypropyl methylcellulose (Methocel K100, MW) in water, 0.5 grams of 20% K90 PVP in water and 0.5 gram of 8% Manugel LBA in water were mixed with 0.245 gram "base solution", 0.0513 gram rizatriptan benzoate and 0.025 gram of aspartame. The degassed mixture was then used for film casting. The film fabrication procedure was the same as above Example 2.

Example 12

HPMC/PVP/Alginate Film 0.66 gram of 6% hydroxypropyl methylcellulose (Methocel K100, MW) in water, 0.60 grams of 20% K90 PVP in water and 1.00 gram of 8% Manugel LBA in water were mixed with 0.245 gram "base solution", 0.0513 gram rizatriptan benzoate and 0.025 gram of aspartame. The degassed mixture was then used for film casting. The film fabrication procedure was the same as above Example 2.

Example 13

HPMC/PVP/Alginate Film 0.66 gram of 6% hydroxypropyl methylcellulose (Methocel K100, MW) in water, 0.80 grams of 20% K90 PVP in water and 0.50 gram of 8% Manugel LBA in water were mixed with 0.245 gram "base solution", 0.0513 gram rizatriptan benzoate and 0.025 gram of aspartame. The degassed mixture was then used for film casting. The film fabrication procedure was the same as above Example 2.

Results for Dissolution in Mouth for Examples 2-13

In-Vivo Retention Study Using Oral Film 2.5 cm$^2$ of film having a thickness of 0.02 cm was applied under the tongue to 6 healthy volunteers. Then, the retention time of film in the mouth without any swallowing and drinking was measured.

Two sites applied were sublingual and buccal area in the mouth. Each site was used for measuring the retention of individual film. The average dissolution time (in minutes) of each Example was shown in the below table 3. Also, the appearance and physical characteristics of films in Examples were also listed in the below table.

TABLE 3

Average Dissolution Time of Films

| | Example | | | | | | |
|---|---|---|---|---|---|---|---|
| | 2 | 3 | 4 | 5 | 6 | 7 | 8 |
| Buccal Film | 8 min 56 sec | 15 min 68 sec | 16 min 33 sec | 17 min 31 sec | 26 min 36 sec | 11 min 15 sec | 8 min 44 sec |
| Sublingual Film | 6 min 66 sec | N/A | 13 min 21 sec | 14 min 34 sec | 16 min 58 sec | 9 min 53 sec | 6 min 34 sec |
| Dried film appearance | light tan, translucent | light tan, translucent | light tan, translucent | light tan, translucent | Opaque | translucent | translucent |

| | Example | | | | |
|---|---|---|---|---|---|
| | 9 | 10 | 11 | 12 | 13 |
| Buccal | 5 min 23 sec | 2 min 35 sec | 5 min 10 sec | 2 min 25 sec | 2 min 12 sec |
| Sublingual | 4 min 14 sec | 2 min 55 sec | 3 min 15 sec | 2 min 10 sec | 1 min 55 sec |
| Dried film appearance | translucent | translucent | translucent, light straw, | translucent, light straw | translucent. light straw |

The following are manufacturing methods of orally disintegrating tablets (ODT).

Method A (Examples 14, 15, 16, 17, 19, 20, 21 and 22.)
1. Dissolve 8 g sucrose ester HLB11 (S-1170) and 3 g sucrose ester HLB5 (S-570) with 20 ml isopropyl alcohol in water bath at 60 C. Then mix with 5 g Tween-80 and 1 g Span-80.
2. Mix 2.5 g ginger oil and 1 g peppermint oil with above solution to become Solution A
3. Prepare PVP K30 solution by dissolving 5 g with 100 ml deionized water
4. Mix 684 g mannitol and 180 g sucrose to become Powder B
5. In a fluidized-bed granulator, spray into Powder B with Solution A and PVP K30 solutions.
6. Continue to dry the resulting mixture in the fludized-bed granulator for 20 minutes until it is totally dried. Pass the dried granulation through a 20 mesh screen.
7. Passage wog rizatriptan benzoate, CMS-Na 5 g, 0.5 g aspartame and 5 g magnesium stearate through 60 mesh screen and then mix them with the above dry granules to yield the final granulation for tableting.
8. Use a tablet machine equipped with 9 mm flat-faced punches to make tablets each weighing 100 mg.

Method B (Example 18)
1. Dissolve 8 g sucrose ester HLB11 (S-1170) and 3 g sucrose ester HLB5 (S-570) with 20 ml isopropyl alcohol in water bath at 60 C. Then mix with 5 g Tween-80 and 1 g Span-80.
2. Mix 2.5 g ginger oil and 1 g peppermint oil with above solution to become Solution A
3. Prepare PVP K30 solution by dissolving 5 g with 100 ml deionized water
4. Prepare 684 g mannitol and 180 g sucrose to become Powder B
5. Add 50 g rizatriptan benzoate to Powder B
6. Prepare granulation by mixing Solution A and PVP K30 solution to Powder B.
7. The wet mass was sieved through a 20 mesh screen and dried at 60 degree C. for 1.5-3 hours. The dried particles were then passed through a 20 mesh screen to prepare dry granules.
8. Pass 50 g rizatriptan benzoate, CMS-Na 5 g, 0.5 g Aspartame and 5 g magnesium stearate through 60 mesh screen and then mix them with the above dry granules.
9. Use a tablet machine equipped with 9 mm flat-faced punches to compress the final granulation into tablets each weighing 100 mg.

Table 4 gives the tablet formulations for the ODTs made by the above procedures. Table 5 presents the dissolution times, the time at which the ODTs were completely dissolved, in the oral cavity for these tablets. All tablets were dissolved in the oral cavity in less than 3 minutes 30 seconds.

Table 6 gives the dissolution profile for the tablets using the official USP procedure using USP apparatus 2 dissolution testing in water at 37° C. and 50 rpm paddle rotation. In USP apparatus 2 dissolution testing, all of the tablets took longer than 5 minutes for complete dissolution with some tablets, Examples 14-18, were not completely dissolved at 30 minutes. In the USP test, the percent is solution was determined by measuring the amount of rizatriptan in solution.

TABLE 4

Formulation of Orally Disintegrating Tablet Examples 14 to 22

| | Example | | | | | | | | |
|---|---|---|---|---|---|---|---|---|---|
| | 14 | 15 | 16 | 17 | 18 | 19 | 20 | 21 | 22 |
| Rizatriptan benzoate | 10 | 10 | 10 | 10 | 10 | 10 | 10 | 20 | 10 |
| S-1170 | | 0.4 | 0 | 0.8 | 0.8 | 0.8 | 0.8 | 0.8 | 1.6 |
| S-570 | | 0.2 | | 0.3 | 0.3 | 0.3 | 0.3 | 0.3 | 0.6 |
| Tween 80 | 1 | 0.3 | | 0.5 | 0.5 | 0.5 | 0.5 | 0.5 | 1 |
| Span 80 | 0.7 | 0.05 | | 0.1 | 0.1 | 0.1 | 0.1 | 0.1 | 0.2 |
| Ginger oil | 0.25 | 0.25 | | 0.25 | 0.25 | 0.25 | 0.25 | 0.25 | 0.5 |
| Aspartame | 0.04 | 0.04 | | 0.04 | 0.04 | 0.04 | 0.04 | 0.04 | 0.08 |
| Peppermint oil | 0.10 | 0.10 | | 0.10 | 0.10 | 0.10 | 0.10 | 0.10 | 0.2 |
| CMC-Na | 0.50 | 0.50 | 0.50 | 0.50 | 0.50 | 0.50 | 0.50 | 0.50 | 0.50 |
| PVP K30 | 0.50 | 0.50 | 0.50 | 0.50 | 0.50 | 0.50 | 0.50 | 0.50 | 0.50 |
| Mannitol/Sucrose (3:1) | 86.41 | 87.26 | 88.5 | 86.41 | 86.41 | 186.41 | 86.41 | 76.41 | 84.32 |
| Mg Stearate | 0.5 | 0.5 | 0.5 | 0.5 | 0.5 | 0.5 | 0.5 | 0.5 | 0.5 |
| Tab weight, mg | 100 | 100 | 100 | 100 | 100 | 200 | 100 | 100 | 100 |
| Thickness (cm) | 0.14 | 0.14 | 0.14 | 0.14 | 0.14 | 0.16 | 0.22 | 0.14 | 0.14 |
| Diameter (cm) | 0.9 | 0.9 | 0.9 | 0.9 | 0.9 | 0.9 | 0.9 | 0.9 | 0.9 |
| sum of Surfactant(%) | 1.7 | 0.95 | 0 | 1.7 | 1.7 | 1.7 | 1.7 | 1.7 | 3.4 |
| Surfactant system HLB | 10.59 | 10.72 | — | 10.72 | 10.72 | 10.72 | 10.72 | 10.72 | 10.72 |

TABLE 5

Dissolution time in oral cavity of ODT

| | Example | | | | | | | | |
|---|---|---|---|---|---|---|---|---|---|
| | 14 | 15 | 16 | 17 | 18 | 19 | 20 | 21 | 22 |
| Oral dissolve time (approx. min) | 3 min 06 sec | 3 min 23 sec | 3 min 07 sec | 3 min 01 sec | 2 min 40 sec | 2 min 46 sec | 3 min 08 sec | 2 min 23 sec | 3 min 09 sec |

TABLE 6

Result of Dissolution Testing for ODT (in water, 37° C., 50 rpm)

| Test | Time (min) | Example | | | | | | | | |
|---|---|---|---|---|---|---|---|---|---|---|
| | | 14 % Dissolved | 15 % | 16 % | 17 % | 18 % | 19 % | 20 % | 21 % | 22 % |
| Dissolution | 2 | 22.31 | 45.65 | 32.30 | 21.54 | 23.32 | 36.06 | 25.06 | 11.53 | 24.50 |
| | 5 | 44.38 | 77.61 | 77.08 | 54.98 | 58.60 | 64.66 | 42.87 | 34.95 | 48.81 |
| | 8 | 60.71 | 81.62 | 76.90 | 77.73 | 89.47 | 98.40 | 69.72 | 60.04 | 74.46 |
| | 15 | 65.86 | 79.94 | 84.06 | 87.17 | 96.17 | 117.80 | 76.63 | 67.39 | 82.64 |
| | 30 | 78.94 | 81.58 | 81.29 | 91.93 | 94.08 | 117.77 | 95.97 | 68.22 | 100.52 |

Pharmacokinetic Study Using Liquid Dosage Formulations

Each of the solutions described in Table 7 were given to a group of six adults by the protocol given in Table 8. Blood levels of rizatriptan were measured a selected intervals by a liquid chromatographic mass spectroscopy procedure.

Samples MG100, MG050 and MG033 did not contain fatty acid esters of sucrose. MG033A contained 0.7% fatty acid esters of sucrose having a combined HLB of 6.71. MG033B contained 0.7% fatty acid esters of sucrose having a combined HLB of 10.71. MG033C contained 0.7% fatty acid esters of sucrose having a combined HLB of 9.36 and also contained surfactants Span 80 and Tween 80 as well as ginger oil which inherently contains a small amount of cineole.

Figure 2:
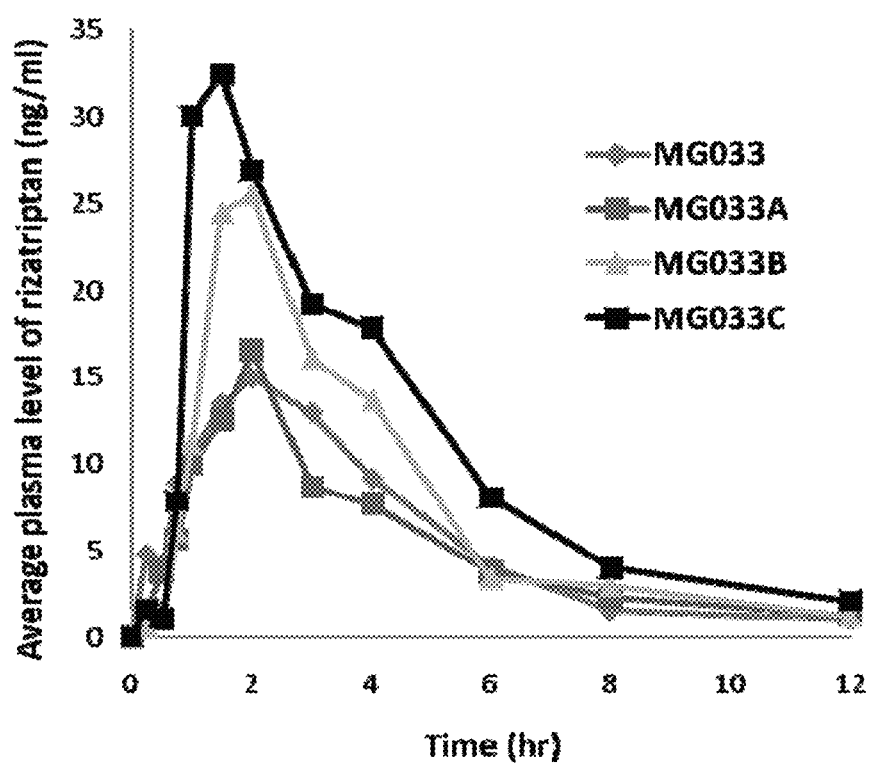
FIG. 2 graphs the plasma levels versus time of rizatriptan after administration resulting from three liquid dosage forms containing the same amount of rizatriptan and absorption enhancers compared with a liquid dosage form containing the same amount of rizatriptan and not containing absorption enhancers.

The data contained in Table 9 and graphically illustrated in FIGS. 1 and 2, demonstrate that the concentration of rizatriptan in plasma is highest from liquid dosage forms containing rizatriptan and one or more fatty acid esters of sucrose having a combined HLB of about 8 to about 16. MG033A-C have the same amount of rizatriptan as active ingredient and identical doses of each was administered. The Cmax is higher for inventive solutions MG033B and MG033C compared to the control MG033 (no absorption enhancer) and MG033A (With absorption enhancer and an HLB of 6.71). Time post dose to maximum blood concentration of rizatriptan (Tmax) is much shorter for MG033C than for MG033 and Mg033A. Area under the curve (AUC) values for the invention solutions MG033B and MG033C are much larger that those of MG033 and MG033A. Area under the curve for inventive compositions MG033B and C is significantly greater than the AUC for MG100 (no absorption enhanser) which contains three times the amount of rizatriptan than the inventive compositions. The AUC for the tablets (table 9) for the commercial ODTs and the swollable tablet is less than the inventive formula MG033A abd MG033B. This is particularly remarkable in that the rizatriptan base dose for the two tablet formulations is 10 mg whereas the dose for MG033A and Mg033B is 6.88 mg rizatriptan base. It was unexpectedly found that dosing or releasing active agent over a period of time resulted in higher peak and AUC plasma levels. The preferred method of administering active agent would be with release over a period of time. A preferred method of treatment releases the active agent over a period of time from about 0.25 minutes to about 15 minutes. A more preferred method of treatment releases the active agent over a period of time from about 0.5 minutes to about 10 minutes. It is believed that at least a fraction of 1% to 80% or greater of the drug (F1) is delivered to and absorbed by the oral mucosa and absorbed systemically and a second fraction of greater than 1% to 80% is delivered to and absorbed along the continuous length of the esophagus and gastrointestinal tract (GIT). Where the first fraction (F1) results in a rapid onset of action and improved bioavailability. Where the second fraction (F2) results in a longer duration of action and improved bioavailability. Where the combined F1 and F2 results in improved bioavailability as seen in the studies.

TABLE 7

Liquid Dosage formulations

| | Group A | | | Group B | | |
|---|---|---|---|---|---|---|
| Ingredients | Ex 23 MG100 % | Ex 24 MG050 % | Ex 25 MG033 % | Ex 26 MG033A % | Ex 27 MG033B % | Ex 28 MG033C % |
| Rizatriptan benzoate | 4.0 | 2.0 | 1.333 | 1.333 | 1.333 | 1.333 |
| S-1170 (HLB 11) | — | — | — | 0.20 | 0.60 | 0.80 |
| S-970 (HLB 9) | — | — | — | — | 0.10 | — |
| S-570 (HLB 5) | — | — | — | 0.50 | — | 0.30 |
| Tween 80 (HLB 15) | — | — | — | — | — | 0.50 |
| Span 80 (HLB 4.3) | — | — | — | — | — | 0.10 |
| Ginger oil | — | — | — | — | — | 0.25 |
| Ethanol | — | — | — | 5.00 | 5.00 | 5.00 |
| Glycerl | — | — | — | 5.00 | 5.00 | 5.00 |
| Aspartame | — | — | — | 0.02 | 0.02 | 0.02 |
| peppermint oil | | | | 0.10 | 0.10 | 0.10 |
| Deionized Water | QS 100 ml | QS 100 ml | QS 100 ml | QS 100 ml | QS 100 ml | QS 100 ml |
| HLB (sum) for sucrose esters | | | | 6.71 (0.7) | 10.71 (0.7) | 9.36 (0.7) |
| HLB (sum) for all enhancers | | | | 6.71 (0.7) | 10.71 (0.7) | 10.72 (1.7) |

TABLE 8

Dosing Protocol

| Group | Formulation | Dose | Administration |
|---|---|---|---|
| A | MG100 | 0.025 ml per every minute | 10 min (1 mg/min) |
| | MG050 | | 20 min (0.5 mg/min) |
| | MG033 | | 30 min (0.33 mg/min) |
| B | MG033A | 0.025 ml per every minute | 30 min (0.33 mg/min) |
| | MG033B | | |
| | MG033C | | |

Total rizatriptan base administered to each subject in Group A and Group B of Table 8 was 6.88 mg.

TABLE 9

Pharmacokinetic Parameters

Pharmacokinetic Parameters
(n = 6 for solution, n = 27 for oral)

| | Test Formula | $C_{max}$ (ng/ml) | $T_{max}$ (hr) | $T_{1/2}$ (hr) | $AUC_{0-2}$ (ng/ml * hr) | $AUC_{0-\infty}$ (ng/ml * hr) |
|---|---|---|---|---|---|---|
| Group A | MG100 | 23.22 | 1.25 | 2.59 | 47.15 | 82.89 |
| | MG050 | 14.61 | 1.71 | 2.52 | 28.91 | 57.78 |
| | MG033 | 18.88 | 1.42 | 3.09 | 18.91 | 73.24 |
| Group B | MG033A | 17.24 | 1.92 | 3.60 | 16.86 | 69.92 |
| | MG033B | 27.08 | 2.08 | 2.52 | 24.82 | 97.12 |
| | MG033C | 38.63 | 1.63 | 2.00 | 36.79 | 132.33 |
| Oral* (10 mg) | ODTs | 20.94 | 1.58 | N/A | 18.83 | 66.13 |
| | Tablet | 27.29 | 0.84 | N/A | 30.03 | 69.88 |

*Adapted from Swan etal, J Clin Pharmacol 2006; 46: 172-178 which is incorporated herein by reference.

A randomized, single-dose, three-period crossover, single-center study in human designed to compare the pharmacokinetic profiles of six (6) different Rizatriptan ODF formulations administered under the sublingual route. All the ODF contained 14.53 mg of rizatriptan benzoate (equivalent to 10 mg rizatriptan), while varying in their ODF film designs. A total of eighteen (18) healthy female subjects were recruited into the study. The subjects were randomly assigned into either Group A or Group B, with nine (9) subjects in each group. In each of the three dosing periods, every subject received one (1) of the three (3) different Rizatriptan ODF prototypes: Example 29, Example 30 and Example 31 for Group A subjects, and Example 32, Example 33 and Example 34 for Group B subjects. The sequence of the three (3) formulations given was arranged in accordance with a randomization scheme. The washout period between each dosing period was 72 hours.

Prior to dosing, all subjects were fasting over night or for at least 8 hours, and were further fasting for additional 4 hours post-dosing. Within 2 hours before and 2 hours after the dosing, the study subjects were refrained from water drinking. The subjects were required not to take caffeine-containing beverage or food at least 3 days prior to the study and during the entire study period. Standard meals were provided to the subjects during the day of dosing in each period.

All Rizatriptan ODF prototypes for use in this pharmacokinetic (PK) study were manufactured and supplied in accordance with the guidelines of Good Manufacturing Practice (GMP).

The six (6) study supply samples, designated as Example 29, Example 30, Example 31, Example 32, Example 33 and Example 34, were all prepared to contain 14.53 mg of rizatriptan benzoate (equivalent to 10 mg rizatriptan). These ODF formulations, however, were formulated to comprise different film forming components and film texture designs. Study supply samples of Example 30, Example 31, Example 32 and Example 33, which consisted of 10% rizatriptan benzoate, were prepared in two identical sheets of the ODF film in a size of 5 cm² per sheet or 10 cm² in total (145 mg as the total weight). Example 29 (14.5% rizatriptan benzoate) was also prepared in two (2) sheets of the ODF film in a size of 3.45 cm$^2$ per sheet or 6.9 cm$^2$ in total (100 mg in weight). Example 34 (14.5% rizatriptan benzoate) was made in one single sheet of the ODF film in a size of 5 cm$^2$ (100 mg in weight). The formulating compositions and sizes of the six (6) ODF formulations are shown in Tables 10 and 11.

TABLE 10

Formulations of Rizatriptan Orally Disintegrated Films (ODFs)

| ODF<br>Targeted Film Size:<br>Ingredients | Example 29<br>100 mg/6.9 cm$^2$<br>mg | Example 30<br>145 mg/10 cm$^2$<br>mg | Example 31<br>145 mg/10 cm$^2$<br>mg |
|---|---|---|---|
| Rizatriptan Benzoate | 14.50 | 14.53 | 14.53 |
| Pullulan | 69.29 | 109.61 | 110.34 |
| Locust bean gum | 0.00 | 0.00 | 0.00 |
| PVP-K90 | 0.00 | 0.00 | 0.00 |
| Na Alginate (Manugel) | 0.00 | 0.00 | 0.00 |
| Sucralose | 1.00 | 1.45 | 1.45 |
| Glycerol | 8.00 | 11.62 | 11.62 |
| S1170 | 4.00 | 4.36 | 4.36 |
| Tween 80 | 2.00 | 2.18 | 2.18 |
| Span 80 | 0.40 | 0.36 | 0.36 |
| Peppermint oil | 0.30 | 0.44 | 0.44 |
| Menthol | 0.50 | 0.73 | 0 |
| FD&C Green #3 | 0.0100 | 0.0145 | 0.0145 |
| Film Weight (mg) | 100.00 | 145.30 | 145.30 |

TABLE 11

Formulations of Rizatriptan Orally Disintegrated Films

| ODF<br>Targeted Film Size:<br>Ingredients | Example 32<br>145 mg/10 cm$^2$<br>mg | Example 33<br>145 mg/10 cm$^2$<br>mg | Example 34<br>100 mg/5 cm$^2$<br>mg |
|---|---|---|---|
| Rizatriptan Benzoate | 14.5 | 14.53 | 14.54 |
| Pullulan | 108.9 | 0.00 | 34.25 |
| Locust bean gum | 0.73 | 0.00 | 0.00 |
| PVP-K90 | 0.00 | 86.87 | 0.00 |
| Na Alginate (Manugel) | 0.00 | 22.74 | 35.00 |
| Sucralose | 1.45 | 1.45 | 1.00 |
| Glycerol | 11.62 | 11.62 | 8.00 |
| S1170 | 4.36 | 4.36 | 4.00 |
| Tween 80 | 2.18 | 2.18 | 2.00 |
| Span 80 | 0.36 | 0.36 | 0.40 |
| Peppermint oil | 0.44 | 0.44 | 0.30 |
| Menthol | 0.73 | 0.73 | 0.50 |
| FD&C Green #3 | 0.0145 | 0.0145 | 0.01 |
| Film Weight (mg) | 145.3 | 145.30 | 100.00 |

Dosage and Administration

All study samples of the ODF prototypes were administered to the study subjects as single dose applications to the sublingual area. The ODF samples of Examples 29 to 33 were administered by stacking two sheets of the ODF film together. Example 34 ODF was applied as one single sheet. Subjects administered the ODF sublingually without water, and were not allowed for water drinking within 2 hours before and 2 hours after the dosing. During the drug administration, all subjects were asked to exercise their best effort to keep the ODF film remained under the tongue and avoid licking the film, and not to swallow saliva until the film was dissolved.

Blood Sampling and Pharmacokientic Analyses

Collection of Biological Samples

During each study period, 5 ml of whole blood samples were collected at designated time: 0 (pre-dose), 15, 30 and 45 minutes, 1, 1.33, 1.67, 2, 3, 4, 6, 8 and 12 hours after dosing. The sampling time might be varied within ±2 minutes at the above mentioned time points. Blood samples were stored in an ice-water bath after collection. Within 5 minutes after sampling, the blood samples were centrifuged at 3,000 g for 8 minutes. Each of the resultant plasma samples was separated into two portions, one was used for drug concentration assay and the other was stored under −20° C.

Pharmacokinetic Parameters

Plasma levels of rizatriptan were determined using a validated LC/MS-MS bio-analytical method.

The pharmacokinetic parameters analyzed in this study included: $AUC_{0-1h}$, $AUC_{0-2h}$, $T_{max}$, $C_{max}$, $T_{1/2}$, $AUC_{0-t}$, and $AUC_{0-\infty}$ for all the six (6) formulations. With reference to a previous PK study on Maxalt® ODT,[7] the study endpoints of the pharmacokinetic analyses in this study were divided into three (3) types: (1) Primary—$AUC_{0-1h}$ and $AUC_{0-2h}$, (2) Secondary—$T_{max}$, and (3) Exploratory—$C_{max}$ and $AUC_{0-\infty}$.

Statistical Analyses

Parameters of $C_{max}$ and AUCs (including $AUC_{0-1h}$, $AUC_{0-2h}$ and $AUC_{0-t}$ and $AUC_{0-\infty}$) were reported in geometric mean values and were analyzed with analyses of variances (ANOVA) after being transformed to a logarithmic scale for pair-wise comparisons between the formulations. Both $T_{max}$ and $T_{1/2}$ were reported in mean and median values. Pair-wise comparisons of median $T_{max}$, or $T_{1/2}$, between study prototypes were performed using a Wilcoxon signed rank test. Pharmacokinetic parameters were analyzed using the DAS Version 2.0 software and statistical analyses were performed using SAS 9.13.

Mouth Residence Time

The mouth residence time of the ODF formulations in each application was observed and reported by the study subjects. The mouth residence time measured the time of the film to be completely dissolved in the sublingual area. The complete dissolution of the film had to be verified by investigator, who confirmed that there were no noticeable gel-like particles of the dissolved film remaining in the sublingual and surrounding area. Mean mouth residence time values between ODF formulations were compared using the student t-test.

Taste

The tastes of the ODF formulations were also assessed in this study. Subjects were required to score the degree of sweetness or bitterness of the study film according to a 10-point scale and to report any tastes they felt from the drug administered. The 10-point scale was from 1 to 10 including, 1=very bitter, 2=moderately bitter, 3=bitter, 4=somewhat bitter, 5=average, very little bitter, 6=average, very little sweet, 7=somewhat sweet, 8=sweet, 9=moderately sweet, and 10=very sweet. Individual taste evaluation results were tabulated and the mean taste scores between prototypes were compared using the student t-test.

Pharmacokinetics

The endpoints of this pharmacokinetic study are summarized in Table 12. All ODF Examples 29 to 34 showed drug concentration profiles with considerably improved absorption of rizatriptan, and exhibited much higher values of $AUC_{0-1h}$, $AUC_{0-2h}$ and $AUC_{0-\infty}$ when compared with those reported for Maxalt® ODT. The geometric mean $AUC_{0-2h}$ values of the ODF formulations were 2 to 2.5 folds of that of the Maxalt® ODT. The results also indicated that ODF formulations exhibited a fast absorption of rizatriptan after sublingual administration. Among the six (6) study prototypes, Example 30 showed the highest $AUC_{0-1h}$ and $AUC_{0-2h}$ values, the designated primary endpoints.

By analyzing the plasma profiles observed in individual subjects, it was interesting to find that there were two (2) absorption peaks in most of the administrations of the ODF formulations (76%, 41/54). The double-peak plasma profile of the ODF was primarily attributable to the two (2) compartmental absorptions of rizatriptan through i) the oral/sublingual cavity and ii) the gastrointestinal tract. For Examples 29 to 34, the median occurrence time of the first peaks (herein defined as $T_{max}$-1) was 0.75 to 1 hour and that of the second peak (herein defined as $T_{max}$-2) was 1.8 to 3 hours (Table 12) in the subjects with double-peak profile.

in pair-wise comparisons between all of the prototypes (p>0.05). However, both the $AUC_{0-1h}$ and $AUC_{0-2h}$ values of all six (6) ODF formulations were considerably higher than those, 2.92 ng/ml·h and 18.83 ng/ml·h, respectively, reported for the Maxalt® ODT in the literature. As described by Swan in the 2006 report on the pharmacokinetics of Maxalt®,[7] the AUC values up to specific time points near $T_{max}$ ($AUC_{0-1h}$ and $AUC_{0-2h}$) would be more meaningful surrogates than the $T_{max}$ itself to evaluate the rate of absorption. The results on the AUC values observed in the first two hours of the ODF

TABLE 12

The Study Endpoints of Pharmacokinetic Parameters Observed for NAL1606 ODF Prototypes

| End Point | Example 29 | Example 30 | Example 31 | Example 32 | Example 33 | Example 34 | Maxalt ® ODT |
|---|---|---|---|---|---|---|---|
| Primary Geometric mean (ng/ml-hr) | | | | | | | |
| $AUC_{0-1\ h\ 0-1\ h}$ | 10.63 | 13.28 | 12.29 | 11.14 | 10.67 | 9.11 | 2.92 |
| $AUC_{0-1\ h\ 0-2\ h}$ | 44.70 | 46.03 | 38.02 | 36.75 | 37.04 | 36.41 | 18.83 |
| Secondary $T_{max\ (h)}$ | | | | | | | |
| Median | 1.67 | 2.00 | 2.00 | 2.00 | 1.67 | 2.00 | 2.92 |
| Mean | 1.67 | 1.89 | 2.01 | 2.11 | 1.53 | 2.37 | 18.83 |
| $T_{max-1\ (h)}$* | | | | | | | |
| Median | 0.75 | 1.00 | 0.88 | 1.00 | 1.00 | 0.88 | 1.33 |
| Mean | 0.88 | 0.79 | 0.93 | 1.08 | 1.18 | 0.94 | 1.58 |
| $T_{max-2\ (h)}$* | | | | | | | |
| Median | 2.00 | 2.00 | 3.00 | 2.50 | 1.84 | 3.00 | |
| Mean | 2.05 | 2.00 | 2.58 | 2.46 | 2.28 | 2.72 | |
| Exploratory Geometric Mean | | | | | | | |
| $AUC_{0-1\ h\ 0-\infty\ (ng/ml-hr)}$ | 180.96 | 158.40 | 149.70 | 132.75 | 123.99 | 150.22 | 66.13 |
| $C_{Max}$ (ng/ml-hr) | 45.22 | 39.12 | 36.05 | 32.50 | 30.81 | 32.24 | 20.94 |
| $C_{Max}^{-1}$ (ng/ml-hr) | 39.00 | 35.38 | 25.93 | 24.95 | 30.98 | 26.47 | |
| $C_{Max}^{-2}$ (ng/ml-hr)* | 43.52 | 38.08 | 33.66 | 28.98 | 28.95 | 30.97 | |

*Subjects N = 6, 7 or 8 for $T_{max}$ − 1, $T_{max}$ − 2, $C_{max}$ − 1 and $C_{max}$ − 2 calculations
**Data from Swan S (2006)

Figure 3:
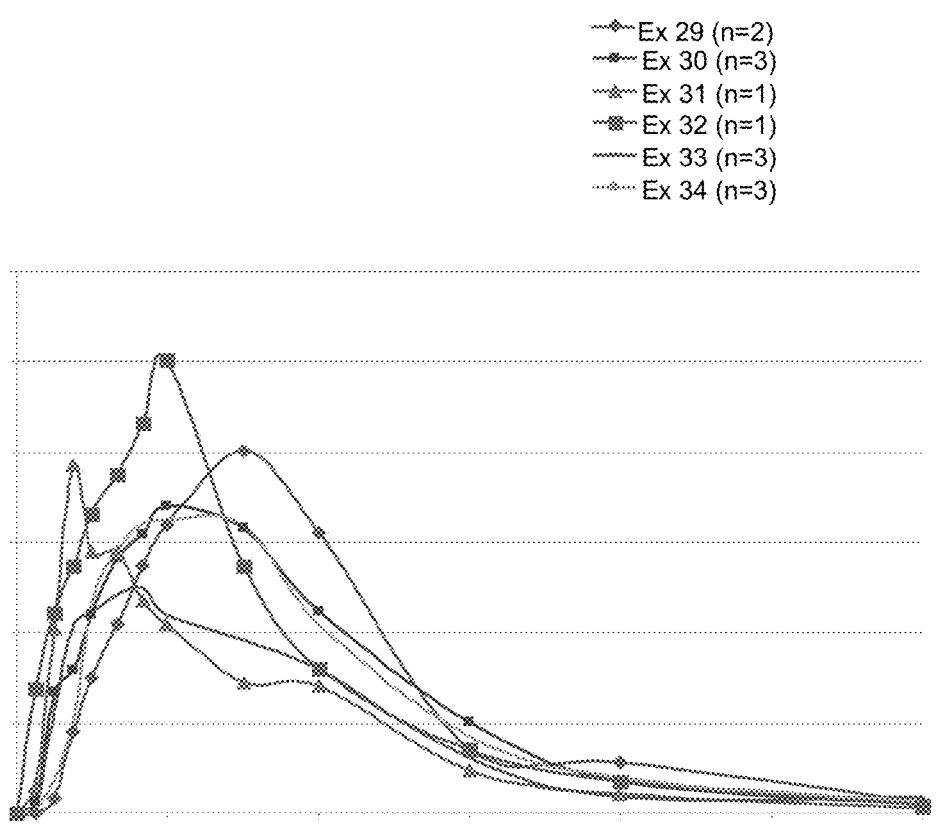
FIG. 3 graphs the plasma levels of rizatriptan versus time after administration of formulations Examples 29 to 34.

In all the subjects, all Examples 29 to 34 reached a mean plasma level of rizatriptan higher than 10 ng/ml at 0.5 hour, and reached approximately 20 ng/ml or higher at 0.75 hour. The mean plasma levels maintained in the range of 24 to 35 ng/ml during 1 to 2 hours, and kept within the range of 19 to 32 ng/ml during 3 to 4 hours, then declined to approximate 10 ng/ml at 6 hours (FIG. 3). It can be seen that both Examples 29 and 30 reached plasma rizatriptan levels at 30 ng/ml or above throughout the time from 1 to 3 hours. The results suggests that the ODF would be able to exhibit an onset of pain relief in as early as 30 to 45 minutes, and could offer a prolonged therapeutic action of at least 4 to 6 hours after a single dose administration. In other words, the ODF may provide a longer duration in efficacy action in comparison to the Maxalt® ODT.

Primary Endpoints: Area-Under-Curve—$AUC_{0-1h}$ and $AUC_{0-2h}$

Among the six (6) ODF formulations, Example 30 showed the highest geometric mean $AUC_{0-1h}$ value (13.28 ng/ml·h) and geometric mean $AUC_{0-2h}$ value (46.03 ng/ml·h). For the other five (5) ODF prototypes, the $AUC_{0-1h}$ ranged from 9.11 to 12.29 ng/ml·h and the $AUC_{0-2h}$ ranged from 36.41 to 44.70 ng/ml·h (Table 12). There were no statistically significant differences in $AUC_{0-1h}$ and $AUC_{0-2h}$ formulations demonstrated that it could provide faster onset, as well as improved bioavailability of rizatriptan, compared with Maxalt® ODT.

Secondary Endpoints: $T_{max}$, $T_{max}$-1, and $T_{max}$-2

The median $T_{max}$ values of the ODF formulations were 1.67 hours for Example 29 and Example 32, and 2 hours for Examples 30, 31, 32 and 34, (Table 12). The median $T_{max}$ values were comparable to that reported in the prescribing information of Maxalt® ODT (1.6 to 2.5 hours). However, as discussed earlier, "double-peak" plasma profiles (FIG. 1) were observed in most of the cases with sublingual administration of ODF. For the analyses, subjects with double-peak in their plasma profiles were identified, and the respective time values to achieve the two peaks ($T_{max}$-1 for the first peak and $T_{max}$-2 for the second peak) and the corresponding maximum peak concentrations ($C_{max}$-1 and $C_{max}$-2, respectively) were analyzed (Table 11.6.1 and 11.6.2). The first peaks usually occurred within the first hour post dosing, with a median $T_{max}$-1 value from 0.75 hr to 1 hour among these prototypes. The second peak was, in general, seen 1 to 2 hours following the first peak, showing a median $T_{max}$-2 value in a range of 1.8 to 3 hours. As the first peaks showed peak concentration values ($C_{max}$-1) in a range of 25 to 39 ng/ml, which were the plasma levels considered as high enough to produce therapeutic effects, therefore, the $T_{max}$-1 values (0.75 to 1 hour) observed should also be considered of clinical significance. The results observed for the early $T_{max}$-1 values collaborated with the results of significantly high $AUC_{0-1h}$ and $AUC_{0-2h}$ values discussed previously, thereby strongly supporting the fast onset profile of the ODF. There were no significant differences in median $T_{max}$ comparisons between these prototypes based on the statistical analyses (p>0.05) (Table 11.12)

Exploratory Endpoints: $AUC_{0-\infty}$, $C_{max}$, $C_{max}$-1, and $C_{max}$-2

As outlined in Table 12, the geometric means of the $AUC_{0-\infty}$ values reported for the ODF were ranging from the least of 123.99 ng/ml·h (NAL1606-205) to the largest of 180.96 ng/ml·h (Example 29). The $AUC_{0-\infty}$ values were more than double when compared with the $AUC_{0-\infty}$ value of 66.13 ng/ml·h reported for the Maxalt® ODT. The results indicated that ODF demonstrated significantly improved bioavailability of rizatriptan through an enhanced absorption of the drug compared with Maxalt® ODT. The geometric mean $C_{max}$ values of ODF formulations showed a range from 30.81 ng/ml (Example 33) to 45.22 ng/ml (Example 29). The $C_{max}$-1 values, the maximum concentrations of the first peak, were reported in a range from 24.95 ng/ml (Example 32) to 390.00 ng/ml (Example 29). The $C_{max}$-2 values, the maximum concentration of the second peak, were slightly higher than $C_{max}$-1, ranging from 28.95 ng/ml (NAL1606-205) to 43.52 ng/ml (Example 29). Example 29 showed the highest $C_{max}$, $C_{max}$-1, and $C_{max}$-2 among the six (6) study formulations. There were statistically significant differences in both the $AUC_{0-\infty}$ and the $C_{max}$ values between Example 29 and Example 33 (each p<0.05), while the differences were insignificant in other pair-wise statistical comparisons of the parameters between other prototypes.

Other Pharmacokinetic Parameters

The mean $T_{1/2}$ ranged from 1.77 hour (Example 32) to 2 hour (Example 29). The ranking of $AUC_{0-t}$ values among the six (6) ODT formulations was in the same order as that observed for the values of the $AUC_{0-\infty}$.

Mouth Residence Time

Mouth residence times of the ODF formulations after sublingual administration were assessed in this study. The mouth residence time refers to the time required for full and complete dissolution of the ODF in the oral cavity. Full and complete dissolution of the ODF is defined as no noticeable gel-like particles of the dissolved film remaining in the oral cavity, rather than simply a breakdown of the film sheet. Usually it may take approximate 1 to 2 minutes to have the whole piece of ODF disintegrated in the mouth after sublingual application, but it would take longer time to see its complete dissolution. In this study, the mean mouth residence times of the ODF ranged from 50.2±1.5 minutes (Example 29) to 8.1±1.1 minutes (Example 33). As a whole, the mouth residence time among all the dosing administrations (n=54) was, in average, 6.6 minutes (Max. 10.5 min; Min. 3 min).

In the previously reported pharmacokinetic study for liquid formulations Tables 7, 8 and 9 above, it was concluded that a mouth residence time of a few minutes up to 10 minutes, rather than a rapid, instant dissolving, would be required for producing faster onset and improved absorption of the drug. The results of this study further verified the findings. A smaller ODF film in the case of Example 29 and a single ODF film in the case of Example 34 showed relatively faster dissolution in mouth, both having a mean mouth residence time significantly different from that of Example 33 (p<0.05). All other ODF comparisons in mouth residence time did not show statistically significant difference (p>0.05).

Taste Evaluation

The tastes of the ODF formulations were evaluated according to a 10-point scale of bitterness/sweetness, which was scored from 1 (very bitter) to 10 (very sweet). The results showed a range of mean taste score from 4.9±1.9 (Example 34) to 6.7±1.7 (Example 32) but no statistical differences between prototypes. As a whole, among all the dosing administrations (n=54), 76% of the subjects reported a score from 5 to 10, representing average to sweet tastes of the ODF formulations. For the 10% loading formulations, i.e. Examples 30, 31, 32 and 33, the percentage of subjects having average to sweet tastes increased to 83%.

The formulations of this study contained peppermint and menthol as the flavoring agents. The taste of the ODF can be variable, by modifying the types of flavors used in the formulation.

Physical dimensions for examples 35 to 46.

Example 35: NAL1606-211, size 2 cm×5 cm, thickness 80-120 μm, weight 145.3 mg.

Example 36: lot 103-6, size 2 cm×1.8 cm, thickness 80-120 μm, weight 40.0 mg.

Example 37: lot 103-11, size 2 cm×1.8 cm, thickness 80-120 μm, weight 40.0 mg.

Example 38: lot 103-22, size 2 cm×2 cm, thickness 80-120 μm, weight 50.0 mg.

Example 39: NAL1619, 3 cm×4.5 cm, thickness 80-120 μm, weight 200 mg.

Example 40: NAL6011-Cetirizine, 2 cm×3.5 cm, thickness 80-120 μm, weight 100 mg.

Example 41. NAL1610-Zolmitriptan, 2 cm×2 cm, thickness 80-120 μm, weight 50.0 mg.

Example 42. NAL1622-Sumatriptan, 3 cm×4.5 cm, thickness 80-120 μm, weight 200 mg.

Example 43. NAL1617K-Ketoprofen, 2 cm×5 cm, thickness 80-120 μm, weight 150 mg.

The above thickness and dimension are approximately measured value averages. The following three examples are predicated values.

(Predicted) Example 44. NAL8817-Donepezil, 2 cm×2 cm, thickness 80-120 μm, weight 50.0 mg.

(Predicted) Example 45. NAL1239-Fentanyl, 2 cm×1.2 cm, thickness 80-120 μm, weight 31 mg.

Example 46. NAL1606-high viscosity: 2 cm×5 cm, thickness 80-120 μm, weight 145.3 mg.

Example 35. NAL1606 Rizatriptan Benzoate ODF

TABLE 13

Formulation NAL1606-211
ODF NAL1606-211
Size/Thickness 2 cm × 5 cm/100 μm
Weight (mg) 145.3 mg

| Ingredients | Dry Film mg | Dry Film w/w % | Wet Formula mg | Workable Formula mg | Working Wet Formula mg | % | 100 gram | |
|---|---|---|---|---|---|---|---|---|
| Rizatriptan Benzoate | 14.53 | 10% | 14.53 | 14.53 | 14.53 | 2.52% | 2.52 | |
| Pullulan | 102.49 | 70.54% | 102.49 | 512 mg 20% Solution | 512 | 89.03% | 89.03 | |
| Purified Water* | 0.00 | 0.00% | 412.87 | 0.00 | | | | |
| Sucralose | 1.74 | 1.20% | 1.74 | 1.74 | 1.74 | 0.30% | 0.30 | |
| Alcohol* | 0.00 | 0.00% | 17.44 | 17.44 | | | | |
| Glycerin | 17.44 | 12.00% | 17.44 | 17.44 | | | | |
| Sucrose Fatty Acid Esters D-1811 | 4.36 | 3.00% | 4.36 | 4.36 | | | | |
| Polysorbate 80 (Tween 80) | 2.18 | 1.50% | 2.18 | 2.18 | | | | |
| Sorbitan Monooleate (Span 80) | 0.36 | 0.25% | 0.36 | 0.36 | 43.95 | 7.64% | 7.64 | g of Intermediate mixture |
| Cherry Flavor | 0.73 | 0.50% | 0.73 | 0.73 | | | | |
| Spearmint Oil | 0.36 | 0.25% | 0.36 | 0.36 | | | | |
| Peppermint Oil | 0.36 | 0.25% | 0.36 | 0.36 | | | | |
| Menthol | 0.73 | 0.50% | 0.73 | 0.73 | | | | |
| FD &C Green #3 | 0.0145 | 0.01% | 0.0145 | 2.9 mg 0.5% solution | 2.906 | 0.50% | 0.50 | |
| Film Weight | 145.30 | 100.00% | 575.61 | | 575.61 | 100.00% | 100 | |

TABLE 14

| Premix A: | |
|---|---|
| Intermediate Ingredients | Weight(g) |
| Ethanol | 6 |
| Glycerin | 6 |
| Sucrose Fatty Acid Esters D-1811 | 1.5 |
| Polysorbate 80 (Tween 80) | 0.75 |
| Sorbitan Monooleate (Span 80) | 0.125 |
| Cherry Flavor | 0.25 |
| Spearmint Oil | 0.125 |
| Peppermint Oil | 0.125 |
| Menthol | 0.25 |

Manufacturing Procedure for NAL1606 Rizatriptan ODF (Dosage Strength: 10 mg):

1. Premix A (Intermediate Mix): Dissolve and mix well sucrose fatty acid esters D1811, glycerin, Tween 80, Span 80, cherry flavor, spearmint oil, peppermint oil, menthol together with ethanol at 60° C.
2. Premix B (20% of pullulan solution): Dissolve pullulan (170.97 g) in water (72.11 g) and mix well at 60° C.
3. Premix C (0.5% of FD & C Green #3): Dissolve 0.1 g of FD&C #3 into 19.9 g of water, mix well.
4. Solution D: Add rizatriptan benzoate into Premix B, mix well.
5. Solution E: Add sucralose into Solution D, mix well.
6. Solution F: Add Premix A into Solution E, mix well at about 60° C.
7. Coating Solution: Add 0.5 g of Premix C into Solution F, mix well at about 60° C.
8. After mixing, deaerate the Coating Solution thoroughly.

Film Forming Process

1. The Werner Mathis AG coating machine was used to cast the films. First the machine was heated to 80° C. The wet film thickness, the gap setting between the doctor knife and the top of a PET film surface, was set between about 0.7 mm to about 1 mm.
2. Mount the PET film to form a smooth flat surface.
3. The degassed coating solution was poured from the solution container across the cross section of the PET film.
4. When ready to coat, the knife was drawn slowly over the coating solution which would spread the solution evenly to form a uniform thickness film.
5. The casted wet film on the PET film was immediately entered the drying compartment of the machine set at about 80° C. for 20 minutes.
6. The dried films were then cut into small films in a size of 2 cm by 5 cm.
7. For PK (Pharmacokinetic) studies, the 2 cm by 5 cm film is further cut into 2 equal pieces of 2 cm by 2.5 cm each.

Example 36

NAL2762 Nicotine ODF

TABLE 15

Formulations NAL2762-102

NAL2762-102 Lot103-6

| ODF Ingredients | Dry Film mg | Dry Film w/w % | Wet Formula mg |
|---|---|---|---|
| Nicotine base | 1.00 | 2.50% | 1.00 |
| Sucrose Fatty Acid Esters D-1811 | 2.00 | 5.00% | 2.00 |
| Alcohol* | 0.00 | 0.00% | 17.00 |
| Pullulan | 31.18 | 77.95% | 31.18 |
| Purified Water* | 0.00 | 0.00% | 132.68 |
| Sucralose | 0.48 | 1.20% | 0.48 |
| Glycerin | 4.00 | 10.00% | 4.00 |
| Polysorbate 80 (Tween 80) | 0.60 | 1.50% | 0.60 |
| Sorbitan Monooleate (Span 80) | 0.10 | 0.25% | 0.10 |
| Peppermint Oil | 0.40 | 1.00% | 0.40 |
| Menthol | 0.20 | 0.50% | 0.20 |
| FD&C Yellow #6 | 0.040 | 0.10% | 0.040 |
| Film Weight | 40.00 | 100.00% | 189.68 |

Example 37

NAL2762 Nicotine ODF

TABLE 16

Formulation NAL2762-103

| ODF | NAL2762-103 Lot 103-11 | | |
|---|---|---|---|
| Dose (mg-Nicotine) | 1.00 mg | | |
| Total ODF | 40.00 mg | | |

| Weight (mg) Ingredients | Dry Film mg | Dry Film w/w % | Wet Formula mg |
|---|---|---|---|
| Nicotine base | 1.00 | 2.50% | 1.00 |
| Alginic Acid | 0.50 | 1.25% | 0.50 |
| Pullulan | 29.48 | 73.70% | 29.48 |
| Purified Water* | 0.00 | 0.00% | 134.38 |
| Sucralose | 0.48 | 1.20% | 0.48 |
| Solutol H15 | 1.00 | 2.50% | 1.00 |
| Sucrose Fatty Acid Esters D-1811 | 1.00 | 2.50% | 1.00 |
| Alcohol* | 0.00 | 0.00% | 5.20 |
| Glycerin | 3.20 | 8.00% | 3.20 |
| Triethyl Citrate | 2.00 | 5.00% | 2.00 |
| Polysorbate 80 (Tween 80) | 0.60 | 1.50% | 0.60 |
| Sorbitan Monooleate (Span 80) | 0.10 | 0.25% | 0.10 |
| Peppermint Oil | 0.40 | 1.00% | 0.40 |
| Menthol | 0.20 | 0.50% | 0.20 |
| FD&C Yellow #6 | 0.04 | 0.10% | 0.040 |
| Film Weight | 40.00 | 100.00% | 179.58 |

Example 38

NAL2762 ODF

TABLE 17

Formulation NAL2762-P01

| ODF | NAL2762-P01 | | |
|---|---|---|---|
| Lot | 103-22 | | |
| Dose (mg)-Nicotine | 1.00 mg | | |
| Total | 50.00 mg | | |

| Weight Ingredients | Dry Film mg | Dry Film w/w % | Wet Formula mg |
|---|---|---|---|
| Nicotine Polacrilex 20% | 5.00 | 10.00% | 5.00 |
| Pullulan | 33.73 | 67.45% | 33.73 |
| Purified Water* | 0.00 | 0.00% | 144.85 |
| Sucralose | 0.60 | 1.20% | 0.60 |
| Glycerin | 7.50 | 15.00% | 7.50 |
| Propylene Glycol | 0.00 | 0.00% | 0.00 |
| Alcohol* | 0.00 | 0.00% | 7.50 |
| Sucrose Fatty Acid Esters D-1811 | 1.50 | 3.00% | 1.50 |
| Polysorbate 80 (Tween 80) | 0.75 | 1.50% | 0.75 |
| Sorbitan Monooleate (Span 80) | 0.13 | 0.25% | 0.13 |
| Peppermint Oil | 0.50 | 1.00% | 0.50 |
| Menthol | 0.25 | 0.50% | 0.25 |
| FD&C Yellow #6 | 0.05 | 0.10% | 0.050 |
| Film Weight | 50.00 | 100.00% | 202.35 |

Physical Properties

TABLE 18

Evaluation of physical properties, taste, and in vivo dissolution of NAL2762 ODF Examples 36, 37 and 38.

| | Code | NAL2762-102 | NAL2762-103 | NAL2762-P01 |
|---|---|---|---|---|
| | Lot # | 103-6 | 103-11 | 103-22 |
| | API | Nicotine base | Nicotine Base | Nicotine polacrilex |
| | Dose of each ODF (mg nicotine) | 1 mg | 1 mg | 1 mg nicotine |
| Physical Attributes | Overall Acceptability | 4 | 2 | 2 |
| | Tear resistance | 4 | 2 | 2 |
| | Flexibility | 3 | 3 | 4 |
| | Tensile strength | 4 | 4 | 1 |
| | Elongation | 0 | 0 | 2 |
| | Rigidity | 4 | 4 | 2 |
| | Film Curved Edges or Wavy | 0 | 2 | 0 |
| | Pencil eraser Tack | 0 | 0 | 0 |
| | Finger tack | 3 | 1 | 3 |

TABLE 18-continued

Evaluation of physical properties, taste, and in vivo dissolution of NAL2762 ODF Examples 36, 37 and 38.

| | Code | NAL2762-102 | NAL2762-103 | NAL2762-P01 |
|---|---|---|---|---|
| | Lot # | 103-6 | 103-11 | 103-22 |
| | API | Nicotine base | Nicotine Base | Nicotine polacrilex |
| | Dose of each ODF (mg nicotine) | 1 mg | 1 mg | 1 mg nicotine |
| | Easy to remove from pouch | 4 | 4 | 4 |
| | Stick to itself | 0 | 0 | 0 |
| Organoleptic | Sweet | 2 | 3 | 3 |
| Attributes | Bitter | 1 | 0 | 0 |
| | Sour | 0 | 0 | 0 |
| | Salty | 0 | 0 | 0 |
| | Other Taste | Peppermint | Peppermint | Peppermint |
| | Mouth Feel | 2 | 3 | 3 |
| | Overall Taste Evaluation | 2 | 3 | 2.5 |
| | In vivo complete dissolution | 3 min 15 sec | 2 min 59 sec | 3 min 06 sec |

Example 39

NAL1619 (Diclofenac Sodium and Rizatriptan Benzoate) ODF

TABLE 19

Formulation NAL1619:

| | Riza-Diclo (NAL1619) | |
|---|---|---|
| Code Ingredients | Dry Film mg | Dry Film w/w % |
| Riza Benzoate | 5.00 | 2.50% |
| Diclofenac Sodium | 20.00 | 10.00% |
| Pullulan | 136.08 | 68.04% |
| Sucralose | 2.40 | 1.20% |
| Ethanol | 0.00 | 0.00% |
| Glycerol | 24.00 | 12.00% |
| D1811 | 6.00 | 3.00% |
| Tween 80 | 3.00 | 1.50% |
| Span 80 | 0.50 | 0.25% |
| Cherry Flavor | 1.00 | 0.50% |
| Spearmint oil | 0.50 | 0.25% |
| Peppermint oil | 0.50 | 0.25% |
| menthol | 1.00 | 0.50% |
| FD &C Green #3 | 0.02 | 0.01% |

TABLE 20

Dissolution Profile of NAL1619ODF Example 39:

Dissolution condition: 50 rpm 37 C, paddle over disk

| Lot | Rizatriptan Benzoate | 1 | 2 | 3 | ave |
|---|---|---|---|---|---|
| 09050601 | 2 | 40.5027 | 38.8877 | 73.536 | 50.975467 |
| | 5 | 90.7091 | 86.0135 | 106.4637 | 94.395433 |
| | 10 | 116.1855 | 104.9442 | 117.6836 | 112.93777 |
| | 15 | 119.3446 | 109.1228 | 121.9668 | 116.8114 |
| | 20 | 122.356 | 113.6185 | 121.0956 | 119.02337 |
| | Diclofenac Sodium | 1 | 2 | 3 | |
| | 2 | 61.7854 | 55.3473 | 86.9744 | 68.0357 |
| | 5 | 99.8688 | 95.9334 | 109.4492 | 101.75047 |
| | 10 | 116.7546 | 108.2991 | 116.3372 | 113.79697 |
| | 15 | 116.6002 | 110.3854 | 117.6814 | 114.889 |
| | 20 | 118.2711 | 113.156 | 118.2983 | 116.57513 |

Example 40

NAL6011-Cetirizine ODF

TABLE 21

NAL6011-101 Formulation

| ODF | NAL6011-101 | | |
|---|---|---|---|
| Size/Thickness | 2cm × 5cm/100 μm 100 mg | | |
| Weight (mg) Ingredients | Dry Film mg | Dry Film w/w % | Wet Formula mg |
| Cetirizine HCL | 10.00 | 10% | 10.00 |
| Pullulan | 69.30 | 69.30% | 69.30 |
| Purified Water* | 0.00 | 0.00% | 326.95 |
| Sorbitol | 5.00 | 5.00% | 5.00 |
| Sucralose | 1.20 | 1.20% | 1.20 |
| Alcohol* | 0.00 | 0.00% | 8.00 |
| Glycerin | 8.00 | 8.00% | 8.00 |
| Sucrose Fatty Acid Esters D-1811 | 3.00 | 3.00% | 3.00 |
| Polysorbate 80 (Tween 80) | 1.50 | 1.50% | 1.50 |
| Sorbitan Monooleate (Span 80) | 0.25 | 0.25% | 0.25 |
| Peppermint Oil | 1.00 | 1.00% | 1.00 |
| Menthol | 0.50 | 0.50% | 0.50 |
| FD &C Yellow #6 | 0.25 | 0.25% | 0.2500 |
| Film Weight | 100.00 | 100.00% | 434.95 |

TABLE 22

Dissolution Profile of NAL6011 Example 40
Dissolution: Medium: Water, Condition: 50 rpm, 37 C. Paddle over disk. Test Method UV
Lot: NAL6011-090581801

|  | 1 | 2 | Ave |
|---|---|---|---|
| Assay | 9.4202 | 9.741 | 9.5807 |

|  | Min | 1 | 2 | 3 | 4 | 5 | 6 | Ave |
|---|---|---|---|---|---|---|---|---|
| Dissolution | 2 | 86.43 | 87.57 | 84.45 | 100.04 | 82.75 | 95.78 | 89.5 |
| 2009.5.21-5.22 | 4 | 96.92 | 100.9 | 106.27 | 103.72 | 96.92 | 107.12 | 102 |
|  | 6 | 103.44 | 108.3 | 111.09 | 109.1 | 103.15 | 105.99 | 106.8 |
|  | 8 | 109.39 | 110 |  |  | 102.59 | 107.12 | 107.3 |

Example 41

Zolmitriptan ODF NAL1610-Lot103-50

TABLE 23

Formulation NAL1610 Example 41
Code: NAL1610
Film: 50 mg

| Ingredients | Dry Film mg | Dry Film w/w % | Wet Formula mg |
|---|---|---|---|
| Zolmitriptan | 2.50 | 5.00% | 2.50 |
| Pullulan | 38.77 | 77.54% | 194 mg of 20% pullulan |
| Sucralose | 0.60 | 1.20% | 0.60 |
| Ethanol | 0.00 | 0.00% | 5.00 |
| Glycerol | 5.00 | 10.00% | 5.00 |
| D1811 | 1.50 | 3.00% | 1.50 |
| Tween 80 | 0.75 | 1.50% | 0.75 |
| Span 80 | 0.13 | 0.25% | 0.13 |
| Peppermint oil | 0.50 | 1.00% | 0.50 |
| menthol | 0.25 | 0.50% | 0.73 |
| FD &C Green #3 | 0.01 | 0.01% | 2.91 mg of 0.5% solution |
| Film Weight | 50.00 | 100.00% |  |

TABLE 24

Physical Property Evaluation of Example 41 NAL1610 ODF

Code: NAL1610
Lot #: 103-50
API and Dosage: 2.5 mg zolmitriptan/50 mg ODF

| Physical Attributes | | |
|---|---|---|
| | Overall Acceptability | 3 |
| | Tear resistance | 3 |
| | Flexibility | 3 |
| | Tensile strength | 4 |
| | Elongation | 0 |
| | Rigidity | 4 |
| | Film Curved Edges or Wavy | 0 |
| | Pencil eraser Tack | 0 |
| | Finger tack | 2 |
| | Easy to remove from pouch | 4 |
| | Stick to itself | 0 |

Example 42

NAL1622-Sumatriptan ODF

TABLE 25

Formulation NAL1622 Example 42
Code: NAL1622-200 mg
Film Weight: 200 mg

| Ingredients | Dry Film mg | Dry Film w/w % | Wet Formula mg |
|---|---|---|---|
| Sumatriptan succinate[1] | 35.00 | 17.50% | 35.00 |
| Pullulan | 130.08 | 65.04% | 650 mg of 20% pullulan in water |
| Sucralose | 2.40 | 1.20% | 2.40 |
| Ethanol | 0.00 | 0.00% | 20.00 |
| Glycerol | 20.00 | 10.00% | 20.00 |
| D1811 | 6.00 | 3.00% | 6.00 |
| Tween 80 | 3.00 | 1.50% | 3.00 |
| Span 80 | 0.50 | 0.25% | 0.50 |
| Peppermint oil | 2.00 | 1.00% | 2.00 |
| menthol | 1.00 | 0.50% | 0.73 |
| FD &C Green #3 | 0.02 | 0.01% | 2.91 mg of 0.5% solution |
| Film Weight | 200.00 | 100.00% |  |

[1]35 mg of sumatriptan succinate is equivalent to 25 mg of sumatriptan base.

TABLE 26

Physical Attributes of NAL1622 Sumatriptan Example 42 ODF:

Code: NAL1622
Lot #: 103-51
API and Dosage: 25 mg sumatriptan/200 mg ODF

| Physical Attributes | | |
|---|---|---|
| | Overall Acceptability | 4 |
| | Tear resistance | 2 |
| | Flexibility | 3 |
| | Tensile strength | 4 |
| | Elongation | 0 |
| | Rigidity | 4 |
| | Film Curved Edges or Wavy | 0 |
| | Pencil eraser Tack | 1 |
| | Finger tack | 3 |
| | Easy to remove from pouch | 4 |
| | Stick to itself | 0 |

Example 43

NAL1617K Ketoprofen ODF

TABLE 27

Formulation NAL1617K Example 43 ODF

| | | | |
|---|---|---|---|
| Code | | NAL1617K-ketoprofen-150 | |
| Film Weight/Size | | 150 mg | |
| Date Ingredients | Dry Film mg | Dry Film w/w % | Wet Formula mg |
| Ketoprofen | 25.00 | 16.67% | 25.00 |
| Pullulan | 98.81 | 65.87% | 494 mg of 20% pullulan in water |
| Sucralose | 1.80 | 1.20% | 1.80 |
| Ethanol | 0.00 | 0.00% | 15.00 |
| Glycerol | 15.00 | 10.00% | 15.00 |
| D1811 | 4.50 | 3.00% | 4.50 |
| Tween 80 | 2.25 | 1.50% | 2.25 |
| Span 80 | 0.38 | 0.25% | 0.38 |
| Peppermint oil | 1.50 | 1.00% | 1.50 |
| menthol | 0.75 | 0.50% | 0.73 |
| FD &C Green #3 | 0.02 | 0.01% | 2.91 mg of 0.5% solution |
| Film Weight | 150.00 | 100.00% | |

TABLE 28

Physical Property of NAL1617K Example 43

| | | |
|---|---|---|
| Code | | NAL1617K |
| Lot # | | 103-54 |
| API and Dosage | | 25 mg ketoprofen/100 mg ODF |
| Physical Attributes | Overall Acceptability | 3.5 |
| | Tear resistance | 2 |
| | Flexibility | 3 |
| | Tensile strength | 4 |
| | Elongation | 0 |
| | Rigidity | 4 |
| | Film Curved Edges or Wavy | 0 |
| | Pencil eraser Tack | 0 |
| | Finger tack | 3 |
| | Easy to remove from pouch | 4 |
| | Stick to itself | 0 |

Examples 44-46 illustrate how one would make an ODF for Donepezil, Fentanyl and Rizatriptan benzoate respectively

Example 44

NAL8817 Donepezil ODF

TABLE 29

Formulation NAL8817 Donepezil ODF Example 44

| | | | |
|---|---|---|---|
| Code | | NAL 8817 Donepezil ODF | |
| Film Weight/Size | | 50 mg | |
| Date Ingredients | Dry Film mg | Dry Film w/w % | Wet Formula mg |
| donepezil hydrochloride | 5.00 | 10.00% | 5.00 |
| Pullulan | 36.27 | 72.54% | 181 mg of 20% pullulan in water |
| Sucralose | 0.60 | 1.20% | 0.60 |
| Ethanol | 0.00 | 0.00% | 5.00 |
| Glycerol | 5.00 | 10.00% | 5.00 |
| D1811 | 1.50 | 3.00% | 1.50 |
| Tween 80 | 0.75 | 1.50% | 0.75 |
| Span 80 | 0.13 | 0.25% | 0.13 |
| Peppermint oil | 0.50 | 1.00% | 0.50 |
| menthol | 0.25 | 0.50% | 0.73 |
| FD &C Green #3 | 0.01 | 0.01% | 2.91 mg of 0.5% solution |
| Film Weight | 50.00 | 100.00% | |

Example 45

NAL1239 Fentanyl ODF Formulation

| No | NAL1239 Ingredients | ODF (Dry Film) (mg) | ODF (Dry Film) (w/w %) | Bulk Coating Solution mg |
|---|---|---|---|---|
| 1 | Fentanyl Citrate | 0.314 | 1 | 0.314 |
| 2 | Pullulan, NF | 24.98 | 79.54 | 24.98 |
| 3 | Purified Water, USP* | 0.00 | 0 | 99.90224 |
| 5 | Sucralose, GRAS | 0.38 | 1.2 | 0.38 |
| 6 | Alcohol, USP* | 0.00 | 0 | 3.00 |
| 7 | Glycerin, USP | 3.77 | 12 | 3.00 |
| 8 | Sucrose Fatty Acid Esters D-1811, | 0.94 | 3 | 0.75 |
| 9 | Polysorbate 80, NF (Tween ® 80) | 0.47 | 1.5 | 0.38 |
| 10 | Sorbitan Monooleate, NF (Span ® 80) | 0.08 | 0.25 | 0.06 |
| 11 | Cherry Flavor, | 0.16 | 0.5 | 0.13 |
| 12 | Spearmint Oil, CDER Listed | 0.08 | 0.25 | 0.06 |
| 13 | Peppermint Oil, NF | 0.08 | 0.25 | 0.06 |
| 14 | Menthol, USP | 0.16 | 0.5 | 0.13 |
| 15 | FD &C Green #3, CDER Listed | 0.00314 | 0.01 | 3.00 |
| | Film Weight | 31.4 | 100.00% | 133.45 |

Example 46

Medium/High Viscosity Water-Ethanol Based Formulation

| ODF Size/Thickness | NAL1606-50% Solid 2 cm × 5 cm/ 100 μm 145.3 mg | | Wet |
|---|---|---|---|
| Weight (mg) Ingredients | Dry Film mg | Dry Film w/w % | Formula mg |
| Rizatriptan Benzoate | 14.53 | 10% | 14.53 |
| Pullulan | 102.49 | 70.54% | 102.49 |
| Water | 0.00 | 0.00% | 100.00 |
| Ethanol | 0.00 | 0.00% | 30.00 |
| Sucralose | 1.74 | 1.20% | 1.74 |
| Glycerin | 17.44 | 12.00% | 17.44 |
| Sucrose Fatty Acid Esters D-1811 | 4.36 | 3.00% | 4.36 |
| Polysorbate 80 (Tween 80) | 2.18 | 1.50% | 2.18 |
| Sorbitan Monooleate (Span 80) | 0.36 | 0.25% | 0.36 |

-continued

| ODF Size/Thickness | NAL1606-50% Solid 2 cm x 5 cm/ 100 μm 145.3 mg | | Wet |
|---|---|---|---|
| Weight (mg) Ingredients | Dry Film mg | Dry Film w/w % | Formula mg |
| Cherry Flavor | 0.73 | 0.50% | 0.73 |
| Spearmint Oil | 0.36 | 0.25% | 0.36 |
| Peppermint Oil | 0.36 | 0.25% | 0.36 |
| Menthol | 0.73 | 0.50% | 0.73 |
| FD &C Green #3 | 0.0145 | 0.01% | 0.0145 |
| Total | 145.30 | 100.00% | 275.30 |

Preparation of Medium/High Viscosity Formulation
1. Premix A (Intermediate Mix): Mix sucrose fatty acid esters D1811, glycerin, Tween 80, Span 80, cherry flavor, spearmint oil, peppermint oil, menthol together with ethanol at 60° C.
2. Premix B: Dissolve pullulan, sucralose and FD&C Green #3 in water, and mix well at 100° C.
3. Solution C: Add rizatriptan benzoate into Premix B, and mix well.
4. Coating Solution D: Combine Premix A and Solution C, mix well at 100° C.

Method to Produce Orally Dissolving Film Dosage Forms from Medium/High Viscosity Formulations The medium/high viscosity Coating Solution D can be further made into orally dissolvable dosage forms using different methods such as extrusion at room temperature or extrusion at slightly elevated temperatures and extrusion particularly through a slot die method by coating onto a support substrate such as polyester to form ribbons, rods, ovoid and other shapes then further processed by drying at 80 to 100° C. and subsequently and cut into unit dosage forms such as films, tablets or lozenges.

Method to Produce Orally Dissolving Dosage Film Forms from High Viscosity Formulations A solvent less polymer carrier formulation composition can be melted by heating at 80 to 200° C. into a high viscosity flowable formulation which can be further made into orally dissolvable dosage forms using different methods such as extrusion (by using single or twin screws or pumping through a slot die) and formed into ribbons, rods, ovoid and other shapes, then cooled to room temperature and cut into unit dosage forms such as films, tablets or lozenges.

We claim:

1. A pharmaceutical composition for application to the oral mucosa comprising:
   a water soluble matrix comprising an effective amount of a pharmaceutically active agent and an absorption enhancer having an HLB of about 8 to about 16,
   wherein the matrix is a film, the absorption enhancer is one or more sucrose fatty acid esters.

2. The pharmaceutical composition of claim 1 wherein the pharmaceutical active agent is selected from the group consisting of anesthetic agents, antitussive agents, nonnarcotic analgesics such as the nonsteroidal anti-inflammatory agent (NSAIDS), erectile dysfunction agents, female sexual dysfunction agents, antihistamine, colds and allergy agents, cough agents, respiratory disorder agents, sore throat agents, respiratory disorder agents, heartburn and dyspepsia agents, antiemetic agents, sleep aids, diarrhea agents, oral hygiene agents, antagonists of CGRP receptors, drugs for hormone replacement, alzheimer's disease agent, caffeine and caffeine salt compounds.

3. The pharmaceutical composition of claim 2 wherein
   a. the anesthetic agent is lidocaine (xylocaine), provacaine, or benzocaine;
   b. the antitussive agent is hexylrescinol or dextromorphine;
   c. the nonnarcotic analgesics such as the nonsteroidal anti-inflammatory agents (NSAIDS) is acetaminophen, Ibuprofen, ketoprofen, indomethacin, aspirin (low dose for cardiovascular), naproxen sodium, ketorolac, diclofenac, meloxicam, or piroxicam;
   d. the erectile dysfunction agent is sildenafil, tadafil, or vardenafil;
   e. the female sexual dysfunction agent is sildenafil, tadafil, or vardenafil;
   f. the antihistamine, cold and allergy agent is certrizine HCl, loratadine, chlorcyclizine HCl, chlorpheniramine maleate, dextrochlorpheniramine maleate, dexbrompheniramine mealate, diphenhydramine citrate, diphenhydramine HCl, doxylamine succinate, phenindamine tartrate, pheniramine, pyrilamine mealate, triprolidine HCl, thonzylamine HCl, or clemastine fumarate;
   g. the cough agent is menthol, camphor, dextromethorphan HBr, guaifenesin, codeine phosphate, or codeine;
   h. the respiratory disorder agent is pseudoephedrine HCl, phenylephrine HCl, guaifenesin, dextromethorphan HBr, or ephedrine;
   i. the sore throat agent is benzocaine, menthol, dyclonine, or phenol;
   j. the heartburn and dyspepsia agent is cimetidine, nizatidine, famotidine, ranitidine, or omeprazole;
   k. the antiemetic agent is graniseton, ondansetron, etc. AZ-001, AZ-004, Levadex, Zelrix, VR-147, ROX-828, COL-144, BF-1, diphenhydramine, or scopolamine;
   l. the sleep aid is zolpidem, Eszopiclone (Lunesta), Zalepon (Sonata), diphenhydramine, doxylamine, benzodiazepines (such as: Estazolam (ProSom), Flurazepam (Dalmane), Temazepam (Restoril), Triazolam (Halcion), or Ramelteon (Rozerem);
   m. the diarrhea agent is loperamide, digestive enzymes (lactase), or bismuth subsalicylate;
   n. the oral hygiene agent is cetylpyridinum chloride, domiphen, thymol, eucalyptol, methyl salicylate, menthol, stannous fluoride, sodium fluoride, benzocaine, phenol, or docosanol;
   o. the drug for hormone replacement is estradiol, or testosterone; and
   p. the Alzheimer's agent is donezapil, galantamine, rivastigmine, tacrin, or memantine.

4. The pharmaceutical composition of claim 1 wherein the pharmaceutically active agent is selected from the group consisting of sildenafil, tadifil, vardenafil, certrizine, donezapil, galantamine, rivastigmine, tacrin, or memantine.

5. The pharmaceutical composition of claim 1 further comprising a nonionic surfactant wherein the combined nonionic surfactant and sucrose fatty acid ester have a combined HLB of about 8 to about 17.

6. The pharmaceutical composition of claim 5 wherein the nonionic surfactant is at least one or more of polysorbate and sorbitan fatty acid ester.

7. The pharmaceutical composition of claim 5 further comprising a secondary absorption enhancer selected from the group consisting of glycerol, ginger oil, cineole and terpenes.

8. The pharmaceutical composition of claim 6 wherein the polysorbate is selected from the group consisting of polyoxyethylene (20) sorbitan monolaurate, polyoxyethylene (20) sorbitan monopalmitate, polyoxyethylene (20) sorbitan and Polyoxyethylene (20) sorbitan monooleate.

9. The pharmaceutical composition of claim 6 wherein the sorbitan fatty acid ester is selected from the group consisting of sorbitan monolaurate, sorbitan monopalmitate, sorbitan monostearate, sorbitan tristearate and sorbitan monooleate.

10. The pharmaceutical composition of claim 1 further comprising a film forming agent selected from pullulan or a polymeric mixture of polyvinyl pyrrolidone and a polymeric alginate.

11. The pharmaceutical composition of claim 10 wherein the film forming agent is pullulan.

12. The pharmaceutical composition of claim 10 wherein the ratio of polyvinyl pyrrolidone to polymeric alginate in the polymeric mixture is from about 5:1 to about 1:3.

13. The pharmaceutical composition of claim 10 wherein the polymeric mixture contains, from about 5% to about 95% by weight of polyvinyl pyrrolidone and from about 5% to about 95% by weight of an polymeric alginate, both of said weights being based on the weight of said polymeric mixture.

14. The pharmaceutical composition of claim 1 wherein said sucrose fatty acid ester is a C12 to C20 saturated fatty acid ester of sucrose.

15. The pharmaceutical composition of claim 1 wherein the sucrose fatty acid esters are selected from the group consisting of sucrose stearate, sucrose palmitate, sucrose laurate, sucrose behenate, sucrose oleate and sucrose erucate.

16. The pharmaceutical composition of claim 1 wherein said sucrose fatty acid ester is a sucrose stearate.

17. The pharmaceutical composition of claim 1 wherein the sucrose fatty acid esters are sucrose fatty acid esters having a monomer content of from about 20 percent to about 80 percent.

18. The pharmaceutical composition of claim 1 wherein said film has a surface area of from 0.25 cm$^2$ to 20 cm$^2$ and a weight of about 1 mg to about 200 mg or a surface area of from 1 cm$^2$ to 10 cm$^2$ about 200 mg and a weight of about 10 mg to 200 mg.

19. The pharmaceutical composition of claim 1 wherein said film contains one or more absorption enhancers in an amount of from about 0.1% by weight to about 20%, about 0.1% by weight to about 15%, or about 1% by weight to about 10% by weight of the film.

20. The pharmaceutical composition of claim 1 wherein said matrix contains an absorption enhancer or a combination of absorption enhancers in a total amount of from about 0.1% by weight to about 20% by weight by weight of the matrix.

21. The pharmaceutical composition of claim 1 wherein the pharmaceutical composition dissolves in the oral cavity in about 0.25 minutes to about 15 minutes.

22. The pharmaceutical composition of claim 1 wherein the film when placed in the oral cavity will dissolve in about 0.25 minutes to about 15 minutes.

23. The pharmaceutical composition of claim 1 wherein the film has a thickness of about 0.01 mm to about 5 mm.

24. A method of drug delivery wherein at least a fraction of 1% to 80% or greater of the drug (F1) is delivered to and absorbed by the oral mucosa and absorbed systemically and a second fraction of greater than 1% to 80% is delivered to and absorbed along the continuous length of the esophagus and gastrointestinal tract wherein the first fraction (F1) results in a rapid onset of action and improved bioavailability and wherein the second fraction (F2) results in a longer duration of action and improved bioavailability such that the combined F1 and F2 results in improved bioavailability, wherein the drug is selected from the group consisting of lidocaine (xylocaine), provacaine, benzocaine, hexylrescinol, dextromorphine, acetaminophen, Ibuprofen, ketoprofen, indomethacin, aspirin (low dose for cardiovascular), naproxen sodium, ketorolac, diclofenac, meloxicam, piroxicam, sildenafil, tadafil, vardenafil, certrizine HCl, loratadine, chlorcyclizine HCl, chlorpheniramine maleate, dextrochlorpheniramine maleate, dexbrompheniramine mealate, diphenhydramine citrate, diphenhydramine HCl, doxylamine succinate, phenindamine tartrate, pheniramine, pyrilamine mealate, triprolidine HCl, thonzylamine HCl, clemastine fumarate, menthol, camphor, dextromethorphan HBr, guaifenesin, codeine phosphate, codeine, pseudoephedrine HCl, phenylephrine HCl, guaifenesin, dextromethorphan HBr, ephedrine, benzocaine, menthol, dyclonine, phenol, cimetidine, nizatidine, famotidine, ranitidine, omeprazole, granisetron, ondansetron, etc. AZ-001, AZ-004, Levadex, Zelrix, VR-147, ROX-828, COL-144, BF-1, diphenhydramine, scopolamine, zolpidem, Eszopiclone (Lunesta), Zalepon (Sonata), diphenhydramine, doxylamine, benzodiazepines (such as: Estazolam (ProSom), Flurazepam (Dalmane), Temazepam (Restoril), Triazolam (Halcion), Ramelteon (Rozerem), loperamide, digestive enzymes (lactase), bismuth subsalicylate, cetylpyridinum chloride, domiphen, thymol, eucalyptol, methyl salicylate, menthol, stannous fluoride, sodium fluoride, benzocaine, phenol, docosanol, estradiol, testosterone, donezapil, galantamine, rivastigmine, tacrin, or memantine.

* * * * *